(12) United States Patent
Brogden et al.

(10) Patent No.: US 10,340,119 B2
(45) Date of Patent: Jul. 2, 2019

(54) AUTOMATED TEM SAMPLE PREPARATION

(71) Applicant: FEI Company, Hillsboro, OR (US)

(72) Inventors: Valerie Brogden, Portland, OR (US); Jeffrey Blackwood, Portland, OR (US); Michael Schmidt, Gresham, OR (US); Dhruti Trivedi, Watervliet, NY (US); Richard J. Young, Beaverton, OR (US); Thomas G. Miller, Portland, OR (US); Brian Roberts Routh, Jr., Beaverton, OR (US); Stacey Stone, Brno (CZ); Todd Templeton, Banks, OR (US)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 15/464,307

(22) Filed: Mar. 20, 2017

(65) Prior Publication Data

US 2017/0256380 A1 Sep. 7, 2017

Related U.S. Application Data

(63) Continuation of application No. 14/934,837, filed on Nov. 6, 2015, now Pat. No. 9,601,313.
(Continued)

(51) Int. Cl.
*H01J 37/302* (2006.01)
*H01J 37/31* (2006.01)
(Continued)

(52) U.S. Cl.
CPC .......... *H01J 37/3023* (2013.01); *G01N 1/286* (2013.01); *H01J 37/28* (2013.01);
(Continued)

(58) Field of Classification Search
CPC ...... H01J 37/3023; H01J 37/28; H01J 37/285; H01J 37/31; H01J 2237/31745
(Continued)

(56) References Cited

U.S. PATENT DOCUMENTS 5,270,552 A 12/1993 Ohnishi et al.
6,405,584 B1 6/2002 Bindell et al.
(Continued)

FOREIGN PATENT DOCUMENTS

JP H0179155 U 5/1989
JP H03230696 A 10/1991
(Continued)

*Primary Examiner* — Nicole M Ippolito

(57) ABSTRACT

Techniques are described that facilitate automated extraction of lamellae and attaching the lamellae to sample grids for viewing on transmission electron microscopes. Some embodiments of the invention involve the use of machine vision to determine the positions of the lamella, the probe, and/or the TEM grid to guide the attachment of the probe to the lamella and the attachment of the lamella to the TEM grid. Techniques that facilitate the use of machine vision include shaping a probe tip so that its position can be readily recognized by image recognition software. Image subtraction techniques can be used to determine the position of the lamellae attached to the probe for moving the lamella to the TEM grid for attachment. In some embodiments, reference structures are milled on the probe or on the lamella to facilitate image recognition.

24 Claims, 18 Drawing Sheets

Related U.S. Application Data

(60) Provisional application No. 62/077,148, filed on Nov. 7, 2014.

(51) Int. Cl.
  *H01J 37/28* (2006.01)
  *H01J 37/304* (2006.01)
  *H01J 37/285* (2006.01)
  *G01N 1/28* (2006.01)

(52) U.S. Cl.
  CPC ........ *H01J 37/285* (2013.01); *H01J 37/3045* (2013.01); *H01J 37/31* (2013.01); *G01N 2001/2873* (2013.01); *H01J 2237/208* (2013.01); *H01J 2237/31745* (2013.01)

(58) Field of Classification Search
  USPC ............. 250/310, 311, 492.1, 492.2, 492.21, 250/492.23, 492.22, 492.3
  See application file for complete search history.

(56) References Cited

U.S. PATENT DOCUMENTS

| | | |
|---|---|---|
| 6,889,113 B2 | 5/2005 | Tasker et al. |
| 2001/0045511 A1 | 11/2001 | Moore et al. |
| 2008/0258056 A1 | 10/2008 | Zaykova-Feldman et al. |
| 2009/0138995 A1 | 5/2009 | Kelly et al. |
| 2010/0305747 A1 | 12/2010 | Agorio et al. |
| 2011/0006207 A1* | 1/2011 | Arjavac .................. G01N 1/32 250/307 |
| 2011/0309245 A1 | 12/2011 | Madokoro et al. |
| 2013/0032714 A1 | 2/2013 | Kitayama et al. |
| 2013/0248354 A1 | 9/2013 | Keady et al. |

FOREIGN PATENT DOCUMENTS

| | | |
|---|---|---|
| JP | H0552721 A | 3/1993 |
| JP | 2000171364 A | 6/2000 |
| JP | 2003156539 A | 5/2003 |
| JP | 2005147671 A | 6/2005 |
| JP | 2007018935 A | 1/2007 |
| JP | 2008210732 A | 9/2008 |
| JP | 2013101123 A | 5/2013 |
| JP | 2014048285 A | 3/2014 |
| WO | WO-2010116428 A1 | 10/2010 |
| WO | WO-2011129315 A1 | 10/2011 |
| WO | WO-2013082496 A1 | 6/2013 |
| WO | 2016002719 A1 | 1/2016 |

* cited by examiner

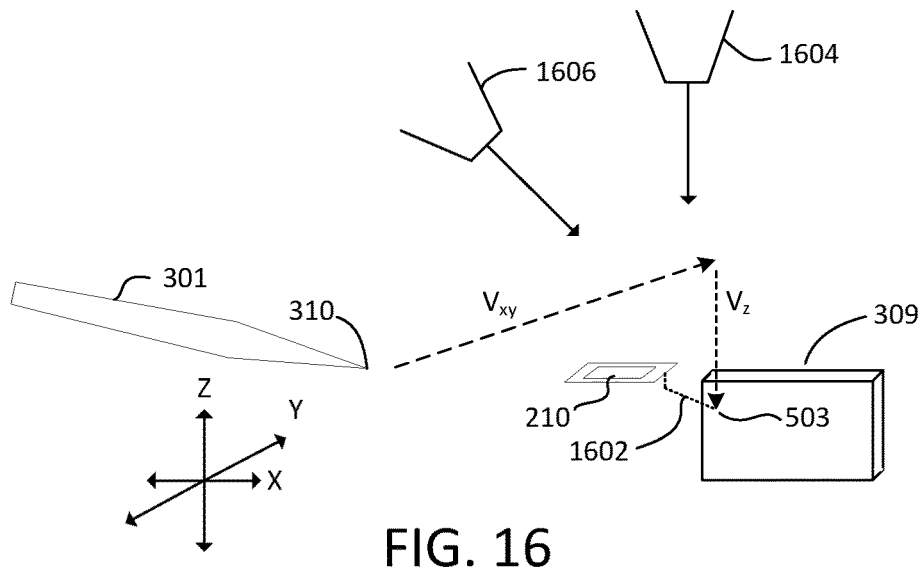
FIG. 16
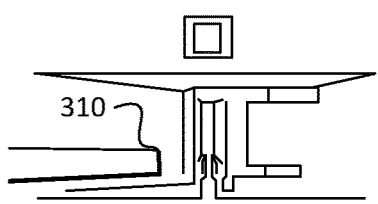    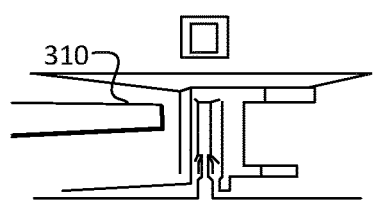    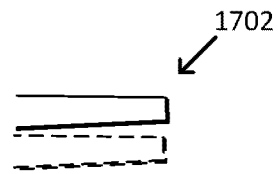
FIG. 17a    FIG. 17b    FIG. 17c
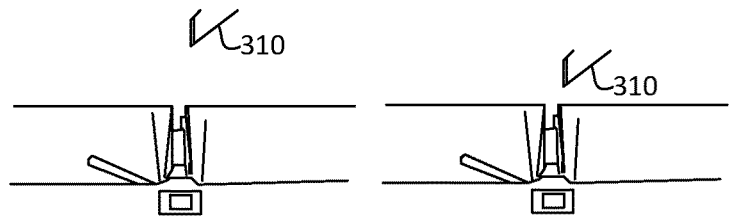    
FIG. 17d    FIG. 17e    FIG. 17f

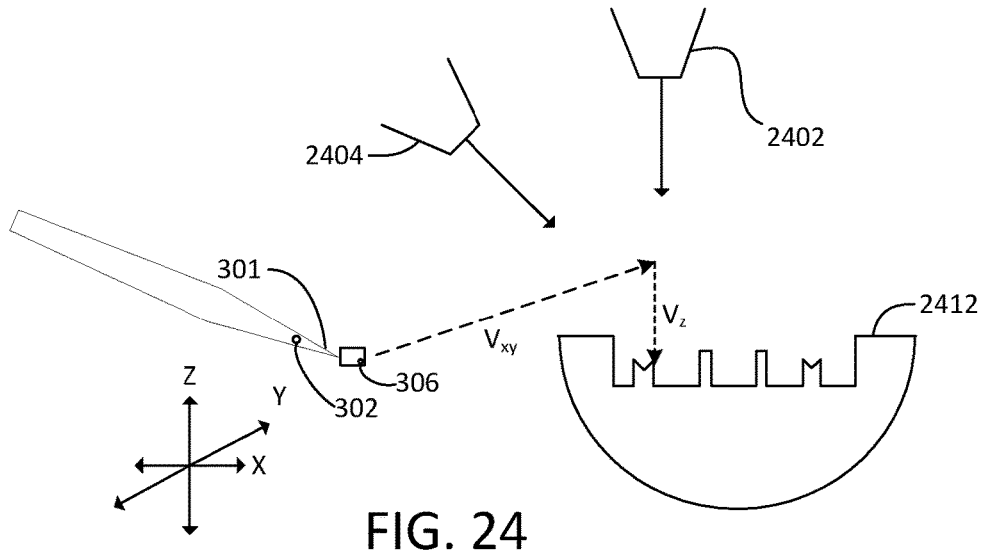
FIG. 24
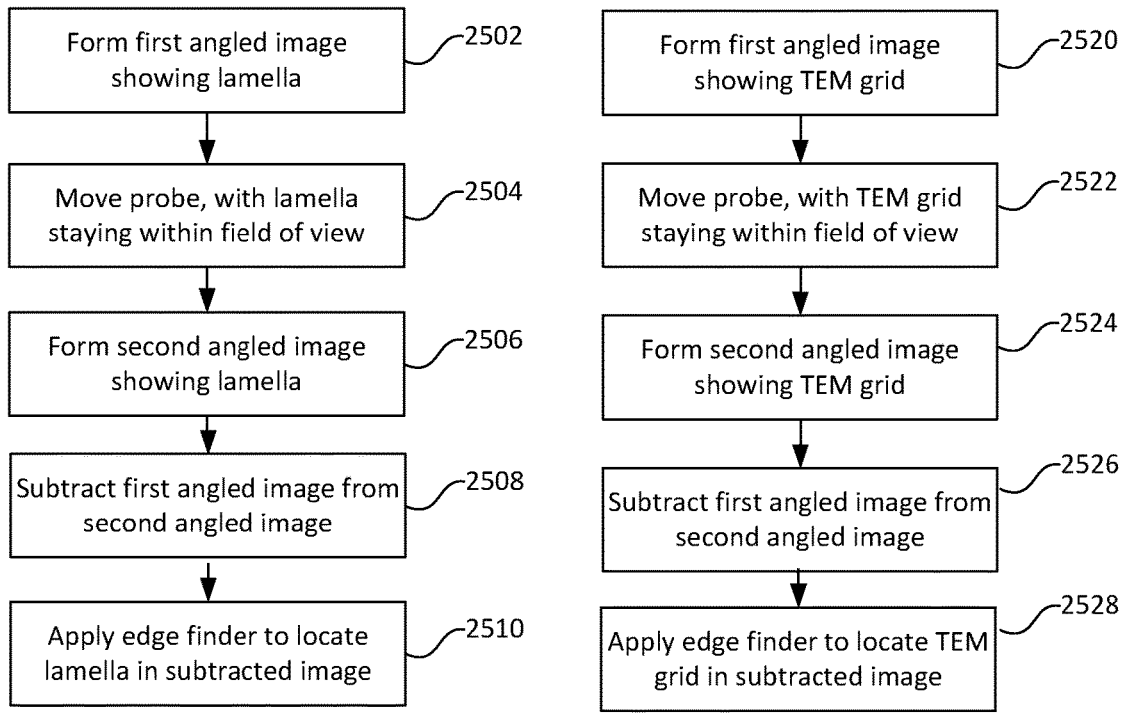
FIG. 25a
FIG. 25b

AUTOMATED TEM SAMPLE PREPARATION

This Application is a Continuation of U.S. patent application Ser. No. 14/934,837, filed Nov. 6, 2015, issued as U.S. Pat. No. 9,601,313, which claims priority from U.S. Prov. Appl. No. 62/077,148, filed Nov. 7, 2014, both of which are hereby incorporated by reference.

TECHNICAL FIELD OF THE INVENTION

The present invention relates to automated preparation of samples for viewing in charged particle beam systems.

BACKGROUND OF THE INVENTION

Semiconductor circuit fabrication methods, as well as other microscopic and nanoscopic manufacturing techniques, have required the development of new imaging techniques, having improved resolution. Improved imaging techniques are also needed in the life sciences. Charged particle beam microscopy, such as electron microscopy and ion microscopy, provides significantly higher resolution and greater depth of focus than optical microscopy. In a scanning electron microscope (SEM), a primary electron beam is focused to a fine spot that scans the surface to be observed. Secondary electrons are emitted from the surface as it is impacted by the primary electron beam. The secondary electrons are detected, and an image is formed, with the brightness at each point on the image being determined by the number of secondary electrons detected when the beam impacts a corresponding spot on the surface. SEMs can also form images from back-scattered electrons as an alternative to secondary electrons. Scanning ion microscopy (SIM) is similar to scanning electron microscopy, but an ion beam is used to scan the surface and eject the secondary electrons. Ion microscopes are also able to form images using secondary ions.

In a transmission electron microscope (TEM), a broad electron beam impacts the sample and electrons that are transmitted through the sample are focused to form an image of the sample. The sample must be sufficiently thin to allow many of the electrons in the primary beam to travel though the sample and exit on the opposite site. Samples are typically less than 200 nm thick and often much thinner.

In a scanning transmission electron microscope (STEM), a primary electron beam is focused to a fine spot, and the spot is scanned across the sample surface. Electrons that are transmitted through the work piece are collected by an electron detector on the far side of the sample, and the intensity of each point on the image corresponds to the number of electrons collected as the primary beam impacts a corresponding point on the surface. The term "TEM" sample as used herein refers to a sample for either a TEM or an STEM and references to preparing a sample for a TEM are to be understood to also include preparing a sample for viewing on an STEM.

Because TEM samples are very thin, preparation of the samples can be delicate, time consuming work. Thickness variations in thin samples, particularly samples less than 100 nm thick, can result in sample bending, over-milling, or other catastrophic defects. The preparation technique determines the quality of structural characterization and the ability analysis of the smallest and most critical structures.

TEM samples can be broadly classified as "cross-sectional view" samples or "planar view" samples, depending on how the sample was oriented on the work piece. If the face of the sample to be observed was parallel to the surface of the work piece, the sample is referred to as a "planar view" or "plan view" sample. If the face to be observed was perpendicular to the work piece surface, the sample is referred to as a "cross-sectional view" sample.

Several techniques are known for preparing TEM samples. Some techniques may involve cleaving, chemical polishing, mechanical polishing, or broad beam low energy ion milling. Combinations of these techniques are also possible. These methods are disadvantageous because they often require that the starting material be sectioned into smaller and smaller pieces, thereby destroying much of the original sample. They are also generally not site specific.

Other techniques generally referred to as "lift-out" procedures use a focused ion beam (FIB) to cut the sample from a substrate while greatly limiting or eliminating damage to surrounding areas of the substrate. These techniques are useful for analyzing the results of semiconductor manufacture, for example. Using lift-out techniques, a sample can be analyzed in any orientation, such as a cross section or plan view. Some techniques extract a sample that is sufficiently thin for use in a TEM without additional preparation. In other techniques the extracted sample is thinned further before observation.

Techniques in which the sample is extracted from the substrate and moved to a sample holder within the FIB vacuum chamber are referred to as "in-situ" techniques. Techniques in which the sample is removed from the work piece and moved to a sample holder after the work piece is removed from the vacuum chamber are referred to as "ex-situ" techniques.

A cross-sectional sample is typically prepared from a larger bulk sample by milling away material with an ion beam to create trenches on either side of the region of interest, leaving a thin section referred to as a "lamella." The lamella is partly severed from the sample substrate by ion beam milling around the bottom and the sides of the lamella until it is connected to the substrate only by a small amount of material. In some cases the connecting material might be "tabs" on either side. In an in-situ process, a sample manipulation probe is then brought in close proximity to the thin sample. The probe is attached to the thin sample, typically by beam-induced deposition of a material from a precursor gas, but other methods can be used, such as electrostatic attachment. Beam deposition can be done with either the FIB or SEM. The material connecting the thin sample to the work piece is then milled away (or mechanically broken) to leave the sample connected only to the manipulation probe. The probe, with the sample attached, can then be moved to a different position where the sample can be attached to a TEM sample holder, called a "grid." The probe is brought very close to a selected part of the TEM grid, and the lamella is attached to the grid, typically by beam-induced deposition. Once the sample has been attached to the grid, the sample probe can be disconnected from the sample, for example, by severing connection with the FIB or merely by moving the probe and/or sample to break the connection. The lamella may be processed further after attachment to the grid.

The process of creating and extracting a lamella and transferring it to the sample grid is a delicate and time-consuming procedure, often requiring about 45 to 90 minutes per sample, and requiring the constant operator attention of a skilled operator. For total analysis of an area of interest on a semiconductor wafer, it may be desirable to analyze as many as, for example, 15 to 50 or more TEM samples. When so many samples must be extracted and measured, the total time to process the samples from one area can be hours or even days. Thus, even though the information that can be gained through TEM analysis can be very valuable, the process has been prohibitively time consuming for manufacturing process control and other routine procedures.

Improving the speed at which lamellae can be prepared for imaging therefore would provide significant advantages in both time and potential revenue by allowing work pieces selected for analysis to return to the production line more quickly. Automation of the lamella preparation process would not only speed up the process but also reduce the level of expertise required for operators, representing an advantage for the manufacturer. In addition, a skilled operator may be performing other tasks while automatic operations are being performed, increasing the throughput of the procedure.

Due to the precision required to mill, extract, transfer, and deposit a lamella on a sample grid, the process has not adapted itself to automation. As the lamella thickness is reduced, it becomes more likely that the region of interest will be excluded from the lamella. Lamellae under 100 nm in thickness, particularly lamellae under 70 nm, are difficult to produce either manually or automatically.

As lamellae becomes thinner, they can warp due to thermal or mechanical stress, changing their positions relative to the beam, which can ruin the lamella by allowing the beam to impact the region of interest. Thickness variations in the lamella can result in sample bending, over-milling, or other catastrophic defects that render the sample useless. In addition, the sample probe for manipulation of the lamella must be placed with extreme precision when preparing to extract the lamella from the substrate, and also when landing the lamella on the sample grid. These factors combine to make the preparation of lamella for analysis an exceedingly difficult process to automate.

SUMMARY OF THE INVENTION

An object of the invention is the automation of part or all of the sample preparation procedure. Because existing manual work flows are difficult to automate, the invention includes new methodologies specifically designed to make automation possible. Sample preparation includes several steps, and this specification describes improvements in several steps. Some embodiments of the invention involve the use of machine vision to determine the positions of the lamella, the probe, and/or the TEM grid to guide the attachment of the probe to the lamella and the attachment of the lamella to the TEM grid. In some embodiments, reference structures known as "fiducials," formed by a charged particle beam on the lamella and/or the probe, can be used to guide the tip to the vicinity of the lamella, and to guide the attachment of the probe to the lamella and the attachment of the lamella to the TEM grid. A fiducial may be formed by milling a structure into the surface or by depositing material onto the surface. Some embodiments use a subtractive imaging routine to locate the lamella and tip using image analysis. Machine identification of the probe tip can be assisted by automatically forming the tip into a consistent shape before attachment to the lamella. The lamella can then be cut free of the work piece and lifted out with the probe. Metrology measurements of the lamella characteristics such as thickness or position can also be used as a feedback mechanism to improve automated performance.

The forgoing has outlined rather broadly the features and technical advantages of the present invention in order that the detailed description of the invention that follows may be better understood. Additional features of and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

FIG. 16 is a diagram showing the geometry of a probe tip approaching a lamella for lift-out;

FIG. 17a-17f are imaging used in the image subtraction method to determine the position of the probe tip relative to the lamella;

FIG. 24 shows the geometry of the lamella approaching the TEM grid;

FIGS. 25a and 25b are flow charts showing the use of image subtraction to determine the difference in the z coordinate between the lamella and the attachment point on the TEM grid;

DETAILED DESCRIPTION OF PREFERRED EMBODIMENTS

Figure 1:
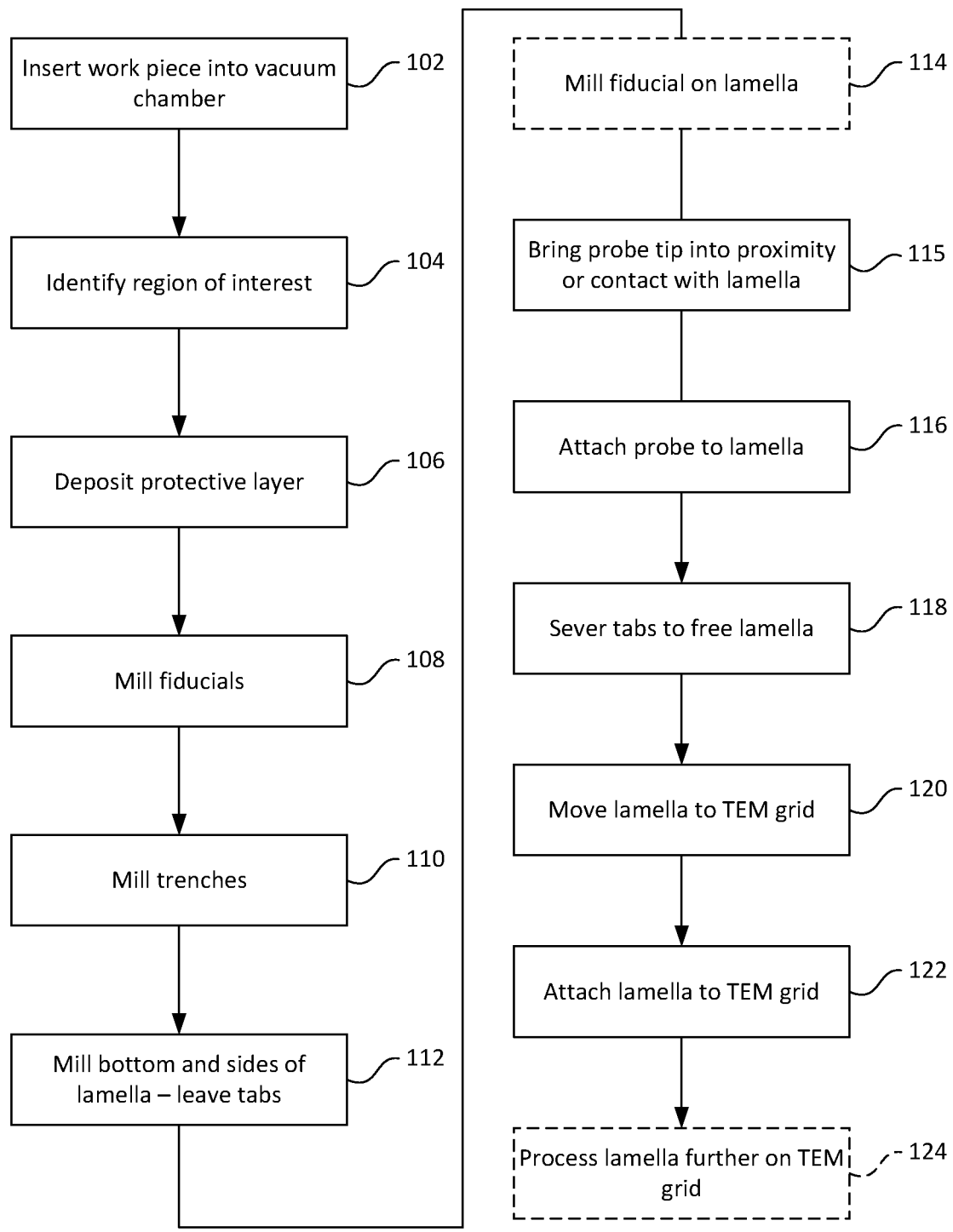
FIG. 1 is a flow chart showing an overview of in-situ lamella formation and extraction.

Preferred embodiments of the present invention are directed to various aspects of the production of thin lamellae for TEM analysis, including their extraction, transport, and subsequent attachment of the lamella to a sample grid for analysis by a fully or partly automated procedure.

The methods described below increase reliability to facilitate automation of each step in the lamella production and preparation.

Some embodiments of the present invention use a dual-beam charged particle system, with a scanning electron microscope (SEM) and a focused ion beam system (FIB) combined to process a sample in a vacuum chamber. The electron beam can produce a high resolution image, while the ion beam can mill the sample to form the lamella. The ion beam is also used for imaging, although the ion beam damages the work piece during imaging. The two beams allow images to be formed from two different perspectives, allowing the position of an object in three dimensional space to be determined from a combination of the images from different perspectives. Both the SEM and FIB are capable of depositing material, and both the SEM and FIB are capable of removing material.

Embodiments of the present invention can be used for the analysis of semiconductor wafers, for quality control and/or failure analysis, as well as for viewing samples in the life sciences, material science and other fields. Often, a region of interest (ROI) is a particular logic cell, which, with modern photolithographic processes, has dimensions on the order of tens of nanometers, and it can be difficult to ensure that the ROI is included within the lamella.

Methods of fabricating a lamella and in-situ sample preparation are described, for example, in U.S. Pat. Pub. No. 2013/0248354, for "High Throughput TEM Preparation Processes and Hardware for Backside Thinning o Cross-Sectional View Lamella" of Keady et al., which application is assigned to the assignee of the present invention and which is hereby incorporated by reference. The present application describes automatable techniques for accomplishing the steps in-situ of sample preparation.

Some embodiments use image recognition software to direct the motion of the probe when automatically attaching the probe to the lamella and/or when attaching the lamella to a TEM grid. There are multiple techniques described herein to facilitate image recognition. Various embodiments can use one or any combination of these techniques. For example, the techniques below describe automatic milling of the probe tip so that the probe tip presents a known appearance that can be readily recognized and the position of the probe tip can be reliably identified. Also described is the milling of a fiducial on the probe, which also allows the position of the probe tip to be reliably identified. Also described is the use of image subtraction techniques to reliably identify the position of an object, such as a probe tip, a lamella, or a TEM grid, using a sequence of images by moving an object of interest between images and then subtracting the images to eliminate the non-moving background. Not all of these techniques will need to be applied in every application. For example, using a probe having a known shape may obviate the need for a fiducial on the probe in some applications. Using subtractive imaging to identify the probe position may eliminate the need for a fiducial on the probe.

Image recognition may use known software metrology tools, such as "edge finders," which are icons having associated functionality and which are placed onto charged particle beam images to recognize an edge within the icon or elsewhere using a change in contrast. Such tools are explained in more detail in U.S. Pat. No. 6,889,113 to Tasker et al. for "Graphical automated machine control and metrology," which is hereby incorporated by reference.

FIB operations can be controlled using graphical software in which a box on the screen can specify an operation to be performed on the portion of the sample shown in the image within the box. Such tools are referred to below as, for example, a "mill box" that specifies the location and beam parameters for milling.

Overview of In-Situ Lamella Extraction Process

Figure 2:
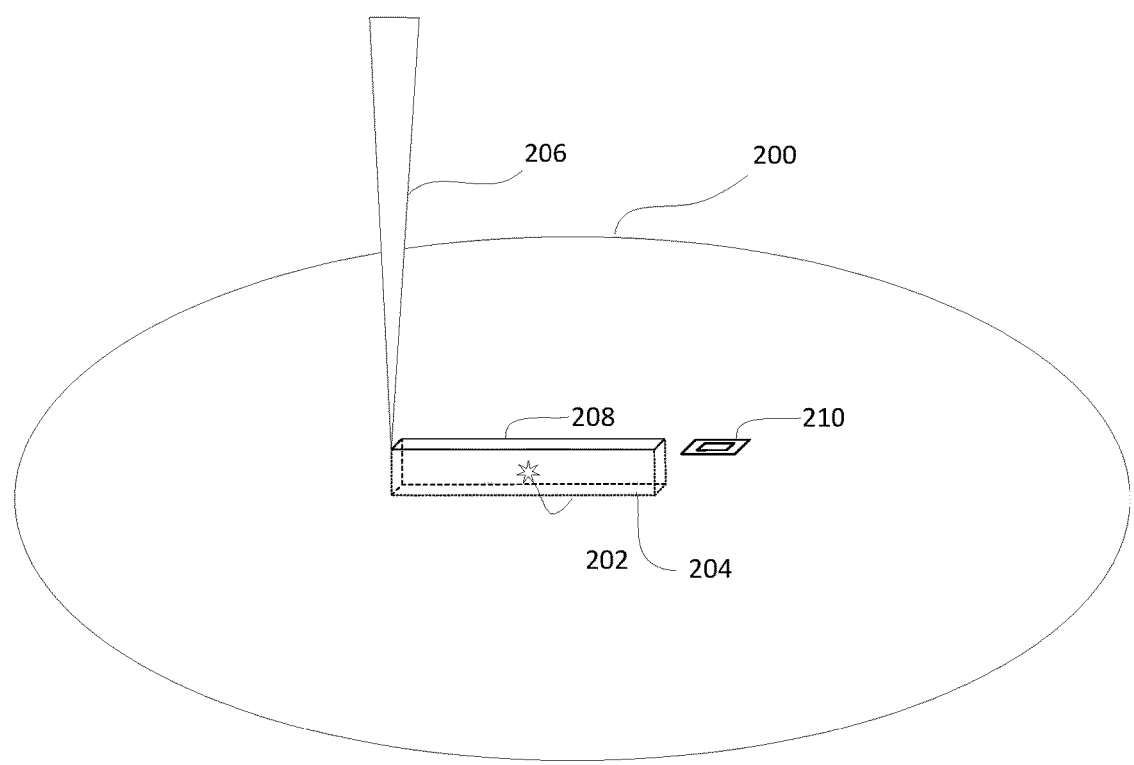
FIG. 2 shows a planned lamella forming operation.

FIG. 1 is a flow chart showing an overview of the steps of an in-situ lamella fabrication process. In step 102, a work piece 200 (FIG. 2), such as a semiconductor wafer, is inserted into a vacuum chamber (not shown) of a dual beam system. In step 104, a region of interest 202 of the work piece is identified, for example, using inspection data, test data, and/or CAD data. FIG. 2 shows the work piece 200 including a volume 204 that includes the region of interest 202. Volume 204 will be formed into a lamella by ion beam 206. In step 106, a protective layer 208 is deposited to protect the region of interest from damage during extraction and thinning of the lamella. In step 108, one or more fiducials 210 are milled adjacent to the region of interest to act as reference points for aligning the ion beam 206 for processing, or for positioning a probe.

Figure 3:
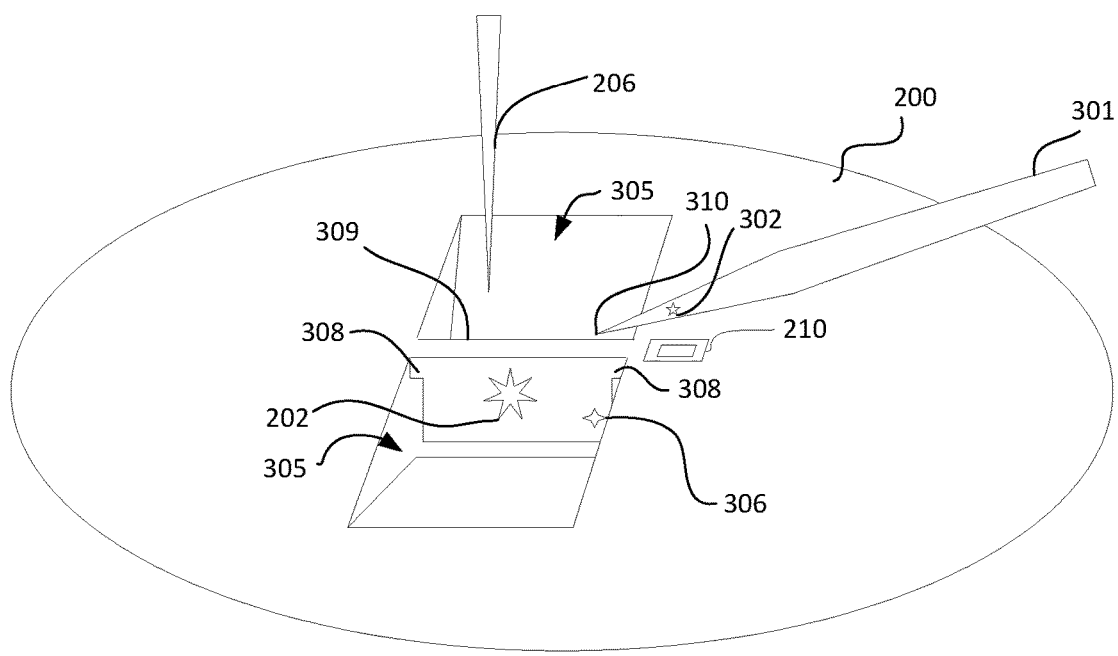
FIG. 3 shows a lamella formed in accordance with the operation of FIG. 2, but not yet been extracted from the work piece.

In step 110, trenches are milled on both sides of the region of interest, leaving a thin lamella 309 as shown in FIG. 3. In some embodiments, an additional cut may be made underneath the lamella using the FIB, so material sputtered during the lamella preparation does not redeposit onto the lamella. FIG. 3 shows a portion of work piece 200 with trenches 305 milled by ion beam 206 to leave lamella 309 containing region of interest 202. Often, a small area or window (not shown) in the lamella is thinned further, leaving the rest of the lamella thick enough to retain mechanical stability. This thinning can be performed before the lamella is extracted from the substrate, while on the needle, or after it is attached to the grid.

In step 112, the ion beam mills around the sides and bottom of the lamella, leaving the lamella attached to the work piece by attachment tabs 308. The location and number of attachment tabs can vary depending on the needs of the work-flow.

Fabricating a Fiducial on the Lamella

Figure 18:
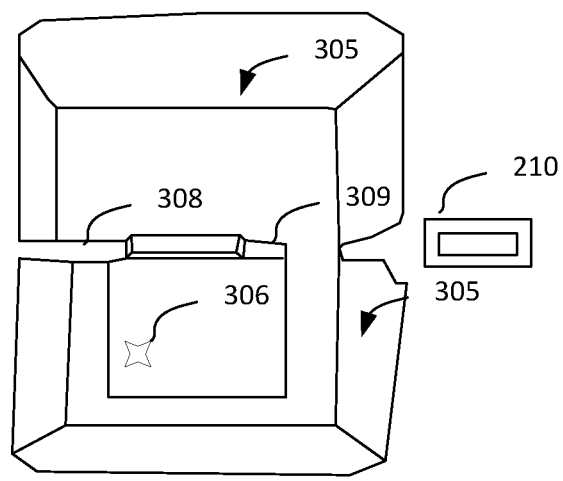
FIG. 18 shows a fiducial milled on a lamella.

In optional step 114, a fiducial 306 is created in the lamella 309. FIG. 18 is a photomicrograph showing a lamella 309 on which a fiducial 306 has been milled. In some embodiments, the fiducial 306 facilitates aligning the lamella 309 with the TEM grid in the X-Y plane, and then landing the grid in the Z direction. A fiducial can be created by milling using the FIB, or by deposition of material using either the FIB or the SEM. Since a fiducial is just a reference target, either deposition or removal can be used to create a fiducial. The fiducial 306 is created in the surface well away from the region of interest and preferably in the section that will be welded onto the TEM grid so that the fiducial does not affect imaging the region of interest. As used herein, the term "weld" refers to adding material via beam-induced deposition to form an attachment, and not, as in metallurgy, to melting the surfaces and adding a filler material that cools to form a bond as in welding metal. A weld can be created by FIB deposition, by SEM deposition, or by some other manner. The fiducial may also be useful during the thinning process to help track how features are evolving as they are thinned. The fiducial could also be useful if trying to do in-situ STEM or when trying to locate a specific gate in a standalone S/TEM.

The shape of the fiducial will vary depending on the work piece. A circle is a good choice for a fiducial for electronics because the features in electronic samples tend to be angular. For life sciences, a square fiducial may be necessary as the features of the sample tend to be round and curvy. The fiducial shape could vary on a case-by-case basis. The fiducial may comprise a shape milled in the surface of the lamella or a hole that extends through the lamella and that has a particular shape.

In some applications, the fiducial improves the success rate of attaching the lamella to the TEM grid because there are no other features to be found in the empty space of the upper half of the FIB image or lower half of the SEM image during grid landing. The fiducial could also be used to fine-tune the rotation alignment of the manipulator by making it easier to precisely locate the lamella after flipping it.

In step 115, a sample probe 301 having a probe tip 310 is brought into contact with or proximity to the lamella 309. Step 115 can be automated using machine vision to find and move the probe tip in relation to the lamella as described below.

Attaching the Probe to the Lamella

Figure 4:
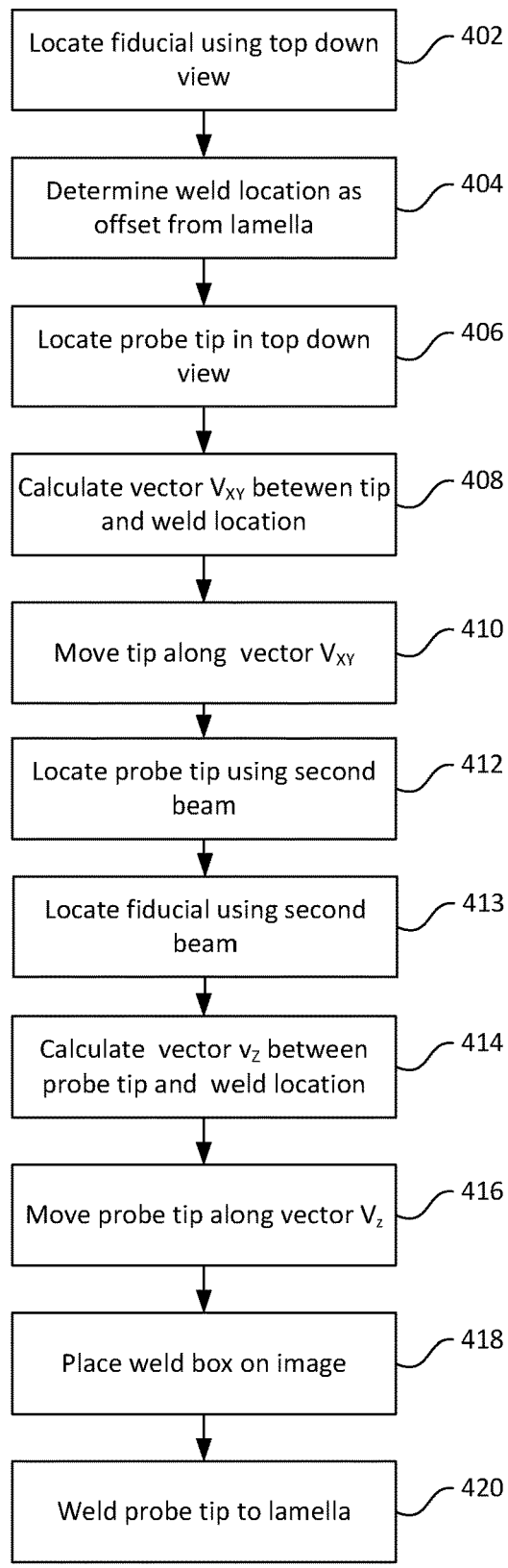
FIG. 4 is a flow chart showing an automated method for attaching a probe to a lamella.
Figure 5:
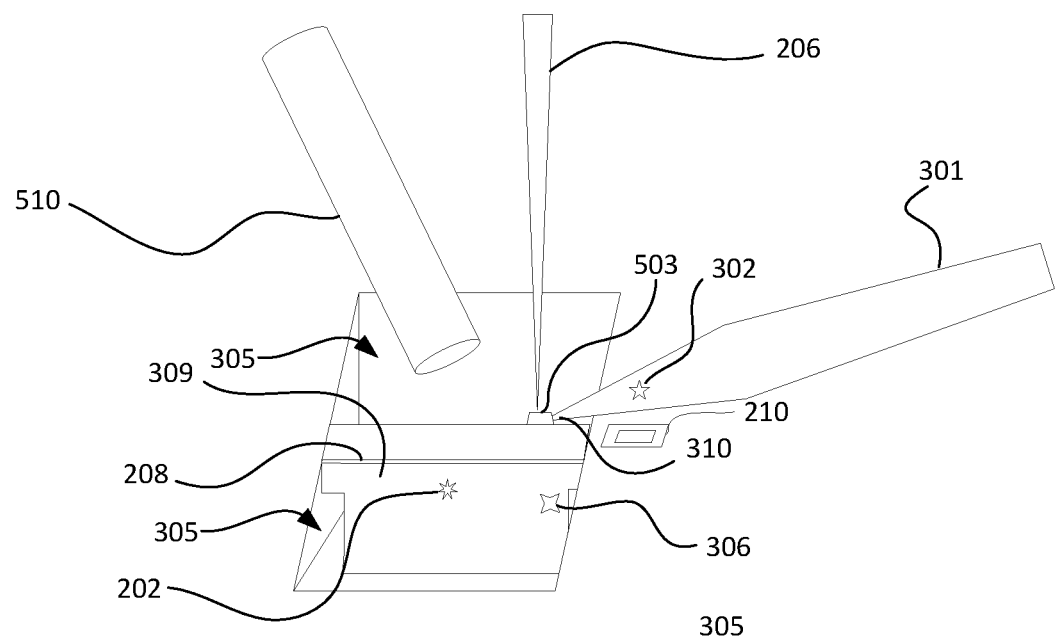
FIG. 5 shows a probe being attached to the lamella of FIG. 3.

FIG. 4 is a flow chart showing a method of automatically attaching the probe tip to the lamella which is illustrated in FIGS. 5 and 16. In some embodiments, the probe tip and attachment point on the lamella are first located in the x-y plane, and the probe tip is moved in the x-y plane to the x-y coordinates of the attachment point. The probe tip and attachment point are then located in an image from a beam that is not orthogonal to the surface so that which the Z coordinates of the probe tip and attachment point can be determined, and the probe tip is moved in the z direction to the attachment point as described below. In other embodiments, the probe could move along a different path to the attachment point and the displacement vector could be calculated differently. "Determining the position of an object" and similar phrases will be understood to include determining the position of an edge of the object or a point on the object, often with the object of moving an edge or point of one object into proximity or contact with an edge or point of another object.

In step 402, fiducial 210 on the work piece by the lamella 309 is located using a top down view generated from an electron beam from electron column 1604. In step 404, the location 503 at which the probe tip 310 is to be welded to the lamella 309 is determined as an offset 1602 from the fiducial 210 since the lamella 309 is located a known distance and a known direction from the fiducial 210. In step 406, the tip 310 of the probe is located in the x-y plane in the top down view from the electron beam column 1604. In step 408, a vector, $V_{xy}$, (FIG. 16) is calculated between the position in the x-y plane of the tip 310 and the position in the x-y plane of the weld location 503 on the lamella, as determined by the offset 1602 from the fiducial 210. In step 410, the probe 301 is moved the calculated vector distance, $V_{xy}$, in a plane parallel to the stage so that the probe is positioned above the lamella face to which the probe will be attached.

In step 412, using an image from the perspective from the tilted ion column 1606 as shown in FIG. 16, the tip 310 of the needle is located. In step 413, the fiducial 210 on the work piece is located. In step 414, a vector, $V_z$, is calculated between the weld location on the lamella, as determined by a known offset from the fiducial 210 and the probe tip 310. In step 416, the probe is moved the calculated vector distance, $V_z$, using motion in the vector normal to the plane of the stage. In determining $V_z$ a trig scalar is used to accommodate for the angled perspective of the ion column 1606. That is, the z distance from the ion beam image is divided by the sine of the angle between the ion beam and a surface normal to determine the magnitude of $V_z$. While FIG. 16 shows the probe attached to the face of the lamella, the probe could also be welded onto the top of the lamella. By welding the probe tip 310 onto a face of the lamella instead of the top of the lamella, the positioning of the probe in the Z direction is less critical. Errors in Z positioning onto the top of the lamella can damage the lamella. If there is a slight gap between the probe tip and the lamella face, the gap is filled in during the weld operation.

Step 116 of FIG. 1, attaching the probe to the lamella, can be accomplished as shown in step 418 by placing a weld box on the image at the position of the probe tip 310 contact with the lamella 309. The program then directs the ion beam column to raster at the weld position using beam parameters suitable for welding by beam-induced deposition. In step 420, the probe tip 310 is welded to the lamella 309. FIG. 5 shows probe tip 310 being attached to lamella 309 by decomposition of a precursor gas, such as $W(CO)_6$, introduced by gas injection nozzle 510 to deposit a material 503. In some embodiments, the probe tip 310 is attached to the top of the lamella. In other embodiments, the probe tip 310 is attached to the face of the lamella, but well away from the region of interest 202. Attaching the lamella to the face, rather than through the top, can be easier for an automated process. The probe can be lowered in the Z direction to a position close to or contacting the lamella and the exact Z dimension of the attachment is not critical, because the probe is not on the top, which has a fixed, single Z value, but on the face which extends in the Z direction.

The procedure then continues with step 118 of FIG. 1, in which the tabs 308 are severed to free the lamella which is attached to the probe 301, from the substrate. In step 120, the lamella is moved to the TEM grid as described in more detail below. In step 122, the lamella is attached to the TEM grid.

Steps 406 and 412 requiring locating the probe in images formed by the beams. This can be performed by image analysis; pattern recognition, or blob finding. Determining proximity or contact between the probe to the lamella can be assisted by using an electrical circuit to detect contact between the probe and the lamella or a capacitance sensor to sense proximity. If the guide method is an image analysis method, finding the probe tip is facilitated by ensuring that the probe tip has a recognizable shape. One method of ensuring that the probe tip has a recognizable shape is to automatically shape the probe tip by ion beam milling.

Shaping the Probe Tip

Figure 6:
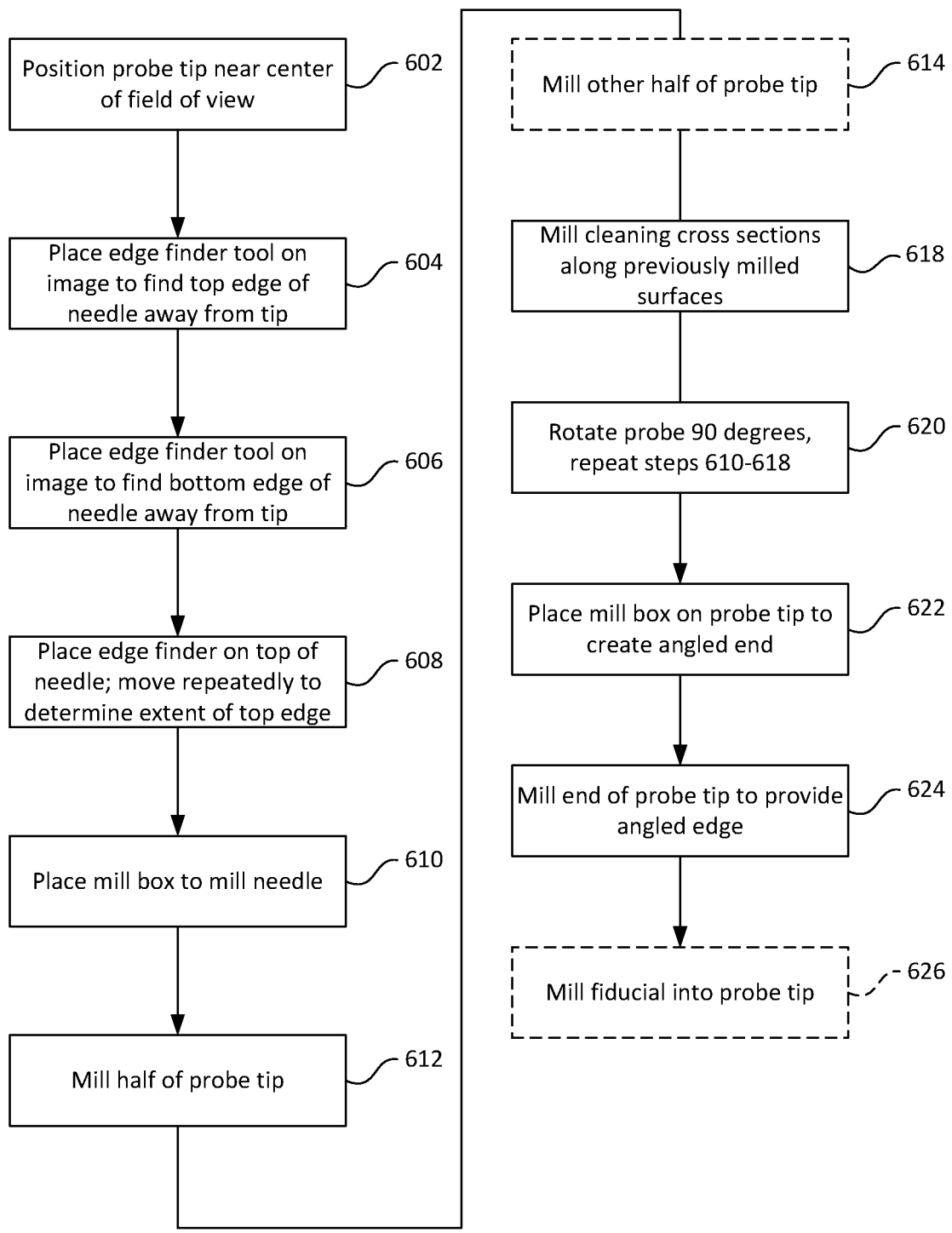
FIG. 6 is a flow chart showing a method for automated shaping of a probe tip.
Figure 7:
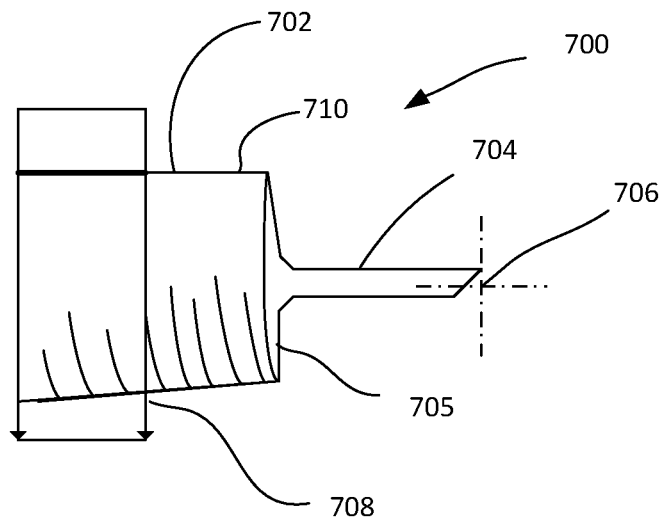
FIG. 7 shows an edge finder applied to find the top of a probe needle.
Figure 8:
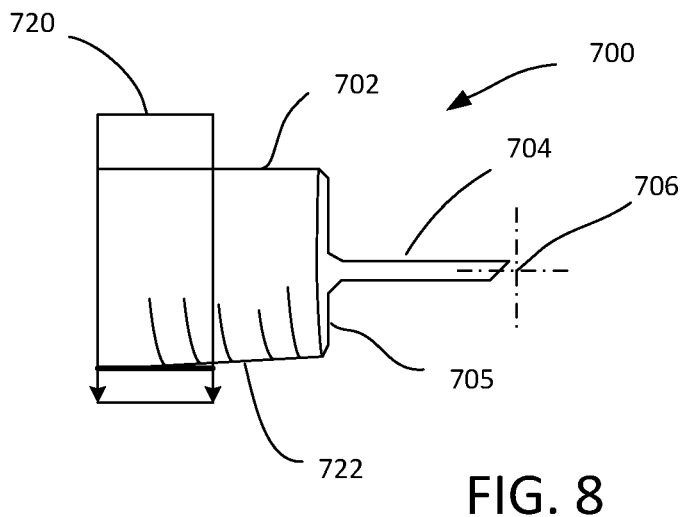
FIG. 8 shows an edge finder applied to find the bottom of the probe needle of FIG. 7.

FIG. 6 is a flow chart showing a method of automatically shaping the probe tip. As shown in FIGS. 7 and 8, the thicker portion of the probe 700 is referred to as the needle 702, the thinned portion is referred to as the tip 704, and the region where the needle transforms into the tip is referred to as the shoulder 705. The needle is typically tapered between about 10 degrees and about 13 degrees, but a straight needle can also be used. In step 602, the probe is moved so that the probe tip is positioned near the center 706 of the field of view of the ion beam. In step 604, an edge finder tool 708 is placed on the image of the needle 702 and used to find the top edge 710 of the needle, as shown in FIG. 7. In step 606, an edge finder tool is place on the image and used to find the bottom edge of the needle, as shown in FIG. 8. Steps 604 and 606 together determine the "Y" location of the needle axis which is ½ way between the top edge and the bottom edge.

Figure 9:
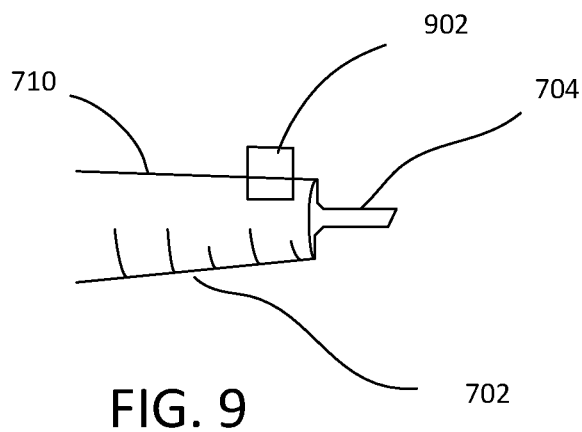
FIG. 9 shows an edge finder used to find the end of the top edge of the needle of FIG. 7.
Figure 10:
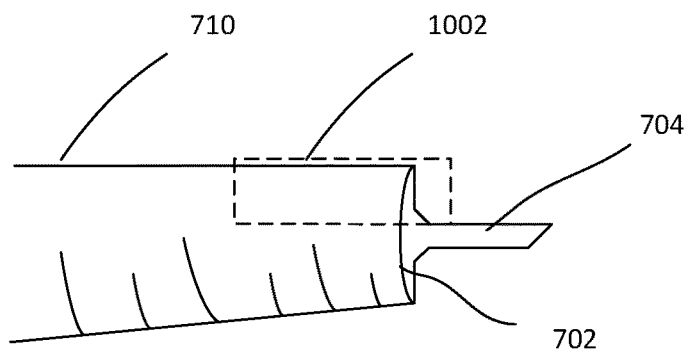
FIG. 10 shows a mill box positioned on the needle to indicate a milling operation on the needle.
Figure 11:
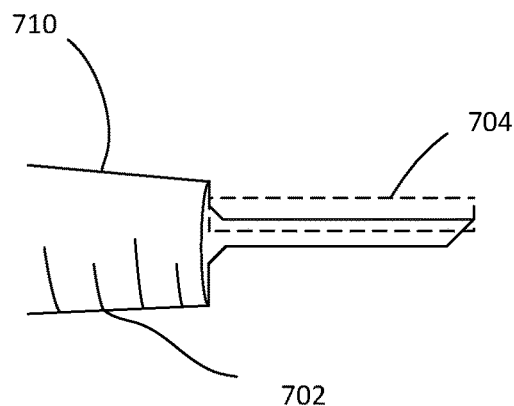
FIG. 11 shows a mill box for applying a cleaning cross section to the surface milled by the mill box of FIG. 10.

In step 608, a shorter edge finder 902 (FIG. 9) that encompasses the top edge, but not the bottom edge, of the needle 702 is repeatedly moved along the top edge of the needle 702 until the edge finder fails, which indicates that the maximum extent of the top edge of the existing needle 702 and the beginning of the tip 704. In step 610, a mill box 1002 (FIG. 10) is placed to mill the needle to create a tip of a desired length and width. The length from the center of the field of view, which corresponds to the end of the existing tip, to the opposite end of the mill box determines the length of the new tip. The distance of the mill box 1002 from the axis of the needle determines ½ the thickness of the new tip. In some embodiments, the tip is preferably less than 10 microns thick, more preferably less than 5 microns thick, even more preferably less than 3 microns thick, and most preferably about 2.5 microns thick. In step 612, the probe from the beginning of the desired tip length to the end of the probe tip 704 is centered in the image. The milling in step 612 is a bulk mill at a high beam current, between 3 nA and 30 nA, more preferably between 5 nA and 20 nA, even more preferably between about 8 nA and 15 nA. In step 614, a similar mill is performed to remove material below the desired probe tip. FIG. 11 shows the needle after the bulk milling is completed to extend the tip length.

After the bulk milling in steps 614, a cleaning cross section is performed in step 618 along the entire length of the probe tip. A "cleaning cross section" is a line mill that slowly advances towards the final cut face position: the beam sweeps back and forth across a line parallel to the desired final cut face and at intervals the line is advanced towards the desired final cut face until it is reached. The intervals are determined by the dose of the mill. The dose is usually measured in nanocoulombs per square micrometer and is essentially a way of defining how many ions impact the work piece per unit area. When using cleaning cross-sections, a dose is typically set that ensures that the material all the way from the top of the cut face down to the bottom of the trench is removed before the line scan is incremented.

Figure 12:
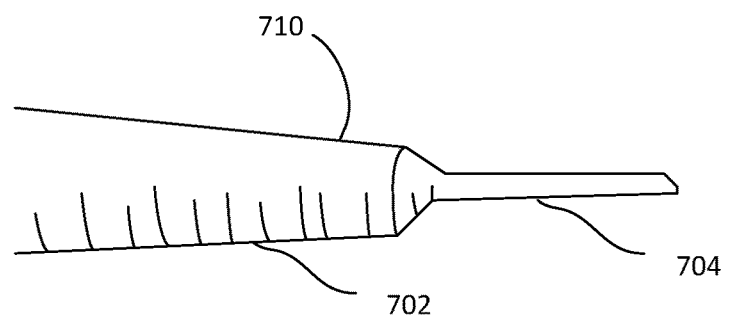
FIG. 12 is a photomicrograph showing the needle after the cleaning cross section applied in FIG. 11.

In step 620, the probe is rotated 90 degrees, and steps 610 to 618 are repeated. The result of the process in FIG. 6 is a probe having a tip of a known length and shaped like a rectangular prism as shown in FIG. 12. Because the needle 702 is tapered, the height of the shoulder between the needle and the tip will increase as the needle is shortened over time during use. Other tip shapes and rotation angles could also be used.

Figure 13:
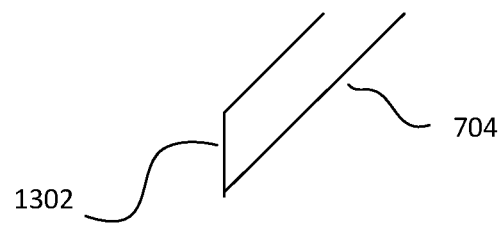
FIG. 13 shows a probe tip cut at an angle.
Figure 14:
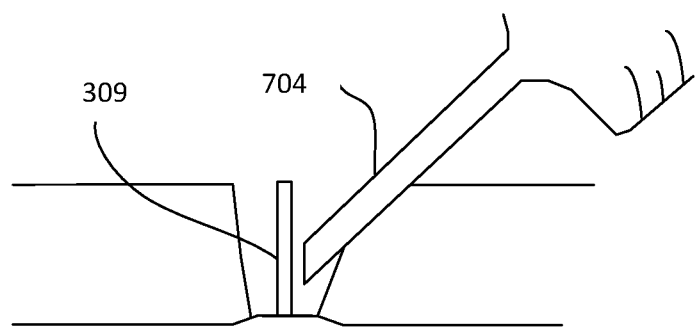
FIG. 14 shows how the angled tip of FIG. 13 engages with a lamella.

Due to the angle between the probe and the substrate when contact is made, it is preferable in some embodiments to mill the end of the probe tip 704 at an angle as shown in FIG. 13. As shown in FIG. 14, then when the probe tip 704 is contacted to the lamella 309, the end of the probe 1302 will be parallel with the face of the lamella 309. The preferred angle at which the probe tip is cut will vary with the angle at which the probe is mounted in the sample chamber. Also, the sharp angles and straight lines easily identified by image recognition software, so this shape improves reliability of image recognition of the probe, as well as improving attachment of the probe to the lamella. The preferred probe tip is therefore "chisel-shaped," that is, the distal edge 1302 is not normal to the long axis and the distal edge does not intersect the long edges at 90 degrees.

Figure 15:
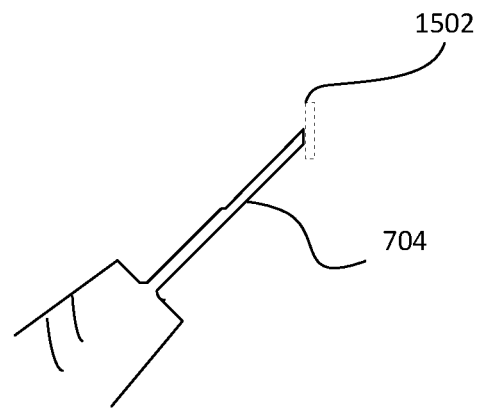
FIG. 15 shows a mill box used to cut the angled tip of FIG. 13.

The chisel-shaped tip may be produced by milling with the ion beam. In step 622, a mill box 1502 applied to the end of the probe tip as shown in FIG. 15 to create the chisel shape. In step 624, the probe tip is milled to provide the angled tip. As a recognizable tip shape is important for image recognition, it may be desirable to maintain the shape of the tip between lamellae. Without accurate information about the location of the edges and tip of the sample probe, it is difficult to calculate the motion path that the probe must take, as described below. The tip is re-formed preferably after each lamella is extracted, or after every two or three lamella are extracted to ensure that the tip shape is recognizable. Often, as lamella are transferred, part of the probe tip is lost with each lamella cut-off, and so the lamella attachment occurs further and further up the tapered probe, causing the shoulder to become higher. The automatic probe re-shaping procedure helps keep the appearance of the probe tip uniform even as the probe becomes shorter.

A key aspect of the automatic probe re-shaping is that it is done "in-situ" inside the particle-beam instrument, as part of the extraction process.

Figure 19:
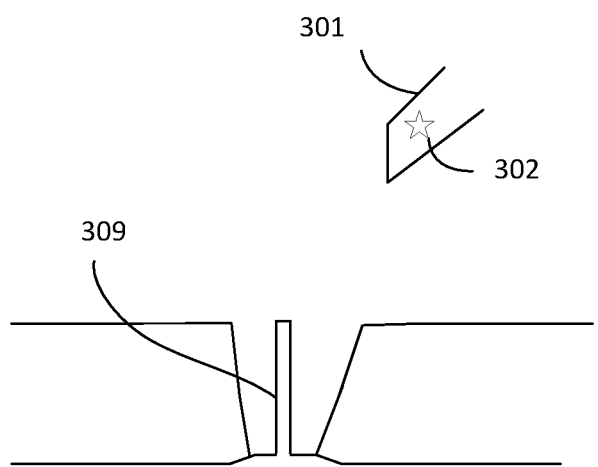
FIG. 19 shows a fiducial milled on a probe tip.

Step 626 shows that a fiducial 302 is optionally milled into the probe tip, as shown in FIG. 3. FIG. 19 shows a fiducial 302 milled onto a probe tip 310. The fiducial may be used to facilitate automatic image recognition of the position of the probe tip to determine the position of the probe tip relative to the lamella in step 115. This fiducial can also be used to refine the area in which the image recognition program looks for the tip, and increases accuracy of the edge finders used. The fiducial can be milled a known distance from the probe tip. When the fiducial is found by image recognition, the probe tip can be located more easily.

The fiducial can be used together with the shaped tip, or in place of the shaped tip, because the fiducial allows a second method of machine recognition of the tip location in an image.

If a fiducial is milled into the probe, when moving the probe tip to the lamella, the position of the fiducial can be used to place an edge finder to locate the end of the probe tip. For example, an edge finder could extend from the end of the fiducial out to a fixed distance, large enough to ensure that the edge is within the search box of the edge finder. The edge finder would locate the edge of the probe tip to facilitate automatically bringing the probe into contact with the lamella by calculating the vector displacement between the probe tip and the lamella. As the lamella is attached to the TEM grid, a new fiducial can be milled in the probe tip to be used when picking up the next lamella.

The fiducial allows the end of the tip to be readily identified by image recognition software so that the needle can be accurately moved to the lamella for welding without damaging the lamella. In some embodiments, a circular fiducial is milled onto the probe tip, although different fiducial shapes can be used. The new fiducial will be used for the picking up the next lamella from the work piece.

As described in this section, the process of shaping a probe tip and/or adding a fiducial to the probe is of particular usefulness in automation of lamella extraction. However, it is not always necessary to perform this process for every lamella extracted. In some cases the probe tip shaping and/or fiducial addition might be performed periodically, but not necessarily for every lamella extracted. For example, the probe tip can be shaped after each lamella is extracted, after every other extracted lamella, after every third extracted lamella, after every fourth lamella or at a greater interval.

Use of Image Subtraction in Bringing Probe Tip to Lamella

Another technique used in some embodiments to facilitate image recognition of specific features in the image is image subtraction. When an image has multiple extraneous features that are unrelated to the task at hand, those features can complicate attempts to automatically locate objects. The extraneous features can be eliminated by taking multiple images in which the target object is moved. The multiple images can be subtracted, which eliminates the stationary extraneous features. The edge finders or other automated metrology tools are placed to determine the location of the object of interest without background interference.

FIGS. 17a-17f show images used to identify the probe tip so that the position of the probe tip can be accurately determined. After the probe tip location is accurately determined, vectors can be calculated to move the probe tip to the lamella weld location for attachment of the probe to the lamella. FIGS. 17a-17c show images from an electron beam that is oriented normal to the work piece surface. These images are used to determine the position of the probe tip in the X-Y plane. FIGS. 17d-17f show images from an ion beam that is oriented at an angle, such as 45 or 52 degrees, to the work piece surface. These images are used to determine the difference in Z coordinate between the probe tip and the attachment point on the lamella.

Figure 20A:
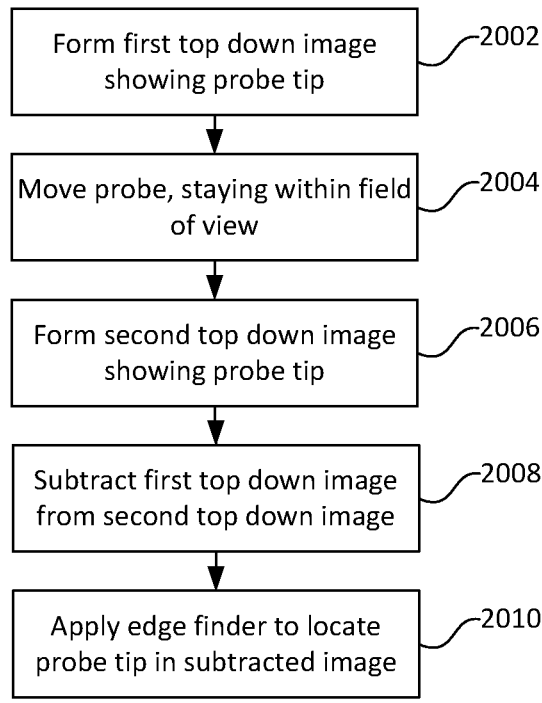
FIGS. 20a and 20b are flow charts showing an image subtraction method for determining the position of the probe tip.
Figure 20B:
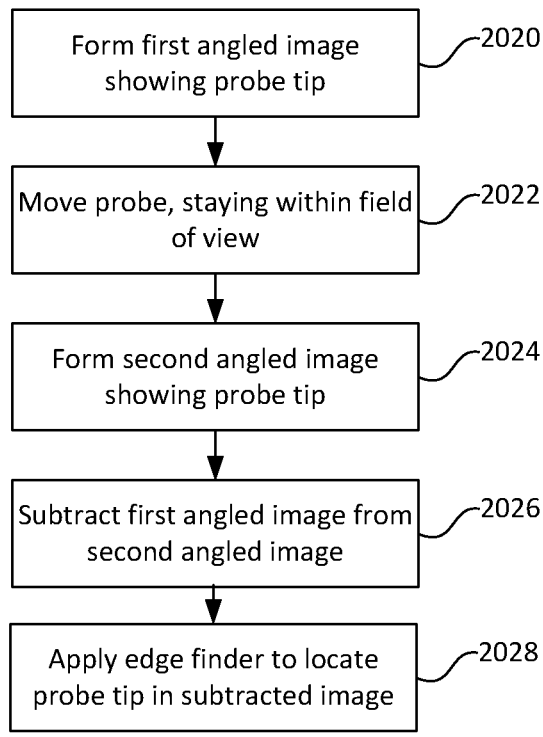

FIGS. 20a and 20b are flow charts showing the use of an image subtraction technique to facilitate automated lift-out. In step 2002 of FIG. 20a, a top-down image is formed of the probe tip 310 as shown in FIG. 17a. In step 2004, the probe is moved a small amount in the x-y plane so that it is still within the field of view of the image taken in step 2002. In step 2006, a second image as shown in FIG. 20b is obtained preferably using the same beam setting as those used to form the image of FIG. 20a. In step 2008, the image of FIG. 17a is subtracted from the image of FIG. 17b. By subtracting images is meant that the gray levels of the pixels in one image are subtracted from the gray level of pixels in the other image. Although the images should be aligned if the beam parameters are unchanged between taking the images, in some embodiments, the images may be aligned before subtraction. In some embodiments, image processing functions, such as; median filter, Gaussian smoothing filter, thresholding, dilation/erosion operations; may be applied to any of the images, before and/or after the subtraction process. FIG. 17c shows the subtracted image 1702, with the contribution from FIG. 17a shown in dashed lines. The background is essentially eliminated, leaving the moved probe tip easier for an edge finder or other metrology tool to precisely locate. In step 2010, an edge finder is applied to the subtracted image in FIG. 17c to locate the probe tip in the subtracted image. The procedure described in FIG. 20 is one method of performing the step of step 406, locating the probe tip in a top down view. Other methods could also be used. In embodiments in which a fiducial is milled on the probe tip, the image subtraction technique can be used to more precisely locate the fiducial. In some embodiments, the use of the image subtraction method eliminated the need for the fiducial on the probe tip. In other embodiments, the fiducial on the probe tip eliminated the need for the image subtraction technique.

Steps 2020 to 2028 of FIG. 20b describe one method of precisely determining the position of the probe tip in the Z direction as indicated in step 412 of FIG. 4. In step 2020, a first image as shown in FIG. 17d is obtained using a beam, an ion beam in this case, that is not oriented normal to the surface. In step 2022, the probe is moved a small amount in the Z direction so that the probe tip is still visible without changing the beam scan area. In step 2024, a second image, FIG. 17e, is obtained using the same beam settings that were used to obtain the image in FIG. 17d. In step 2026, the image of FIG. 17d is subtracted from the image of FIG. 17e to show in FIG. 17e the change in position of the probe tip and eliminate the image of the work piece surface to facilitate recognition of the probe tip. In step 2028, an edge finder is used to locate the probe tip in the image of FIG. 17f. After the probe tip is located in the Z direction, the position can be used to determine the vector $V_z$ in step 414.

For the case of identifying a probe, having two images obtained, with only the probe moving a small amount relative to the image, allows one to subtract the images and determine a boundary associated with the outer envelope of the tip. Such a process greatly assists in determining the location of the probe envelope. Multiple motions can be performed to obtain additional information. It can also be advantageous to move known amounts, and make use of the known motion amount as part of the analysis.

Attaching the Lamella to the TEM Grid

Figure 21:
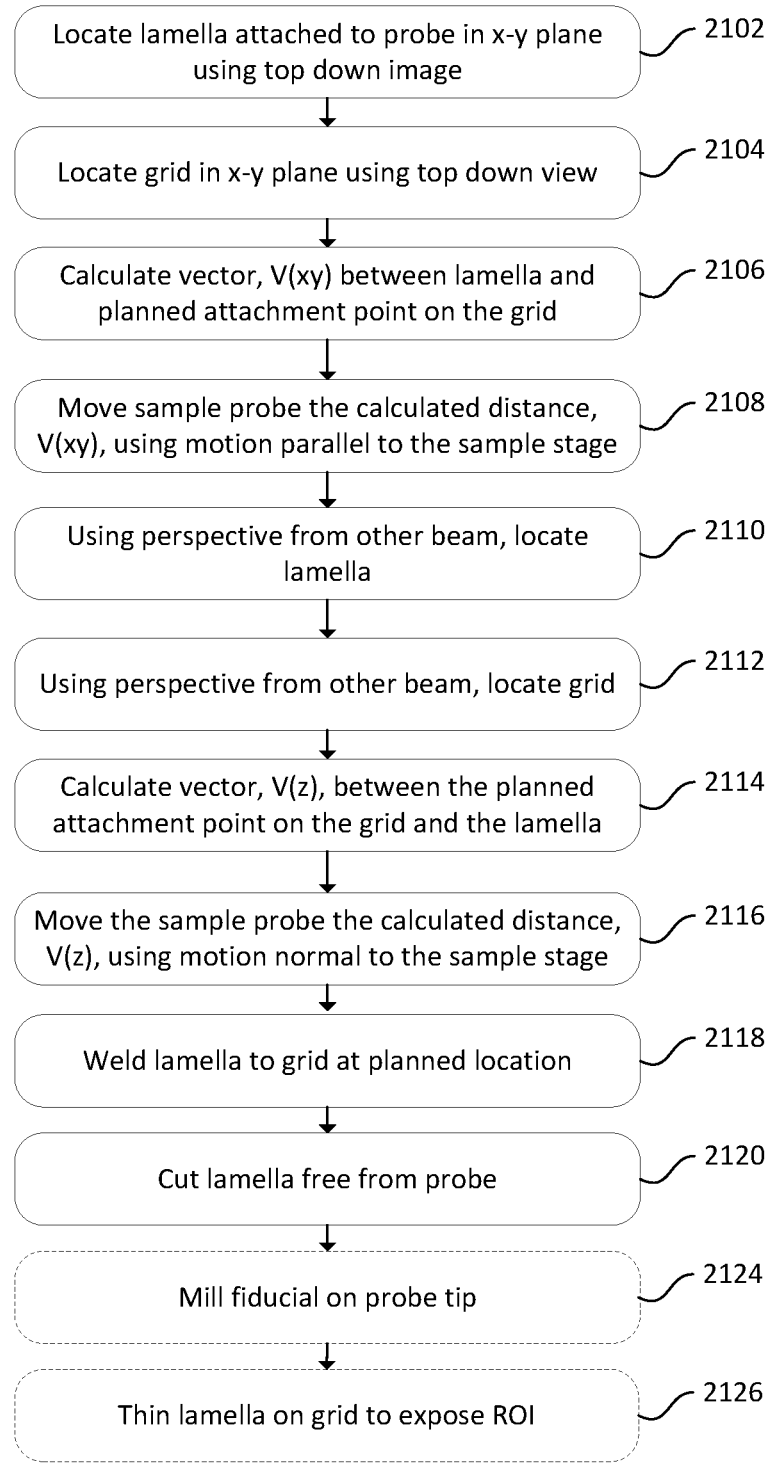
FIG. 21 is a flow chart showing a method of attaching a lamella to a probe.

FIG. 21 is a flow chart describing the process of attaching the lamella 309, which is attached to probe 301, to a TEM grid. As will be understood, TEM grids are structures on which the lamellae are mounted for viewing on a TEM and are commercially available from the applicant. For accurate landing of the lamella on the grid, accurate locations of the probe with attached lamella and the grid should be known in all three dimensions. For three-dimensional location, the perspective of a second beam at an angle to the first beam can be used. The image subtraction routine of FIGS. 22a and 22b can be used to identify the locations of the probe with attached lamella and the sample grid using the second perspective.

In step 2102, the lamella 309 is located. In some embodiments, the lamella is located automatically using pattern recognition software. The pattern recognition could be facilitated by a fiducial 306 on the lamella as shown in FIG. 18 to facilitate locating the lamella. Locating the lamella could also be facilitated using subtractive imaging.

Figure 22A:
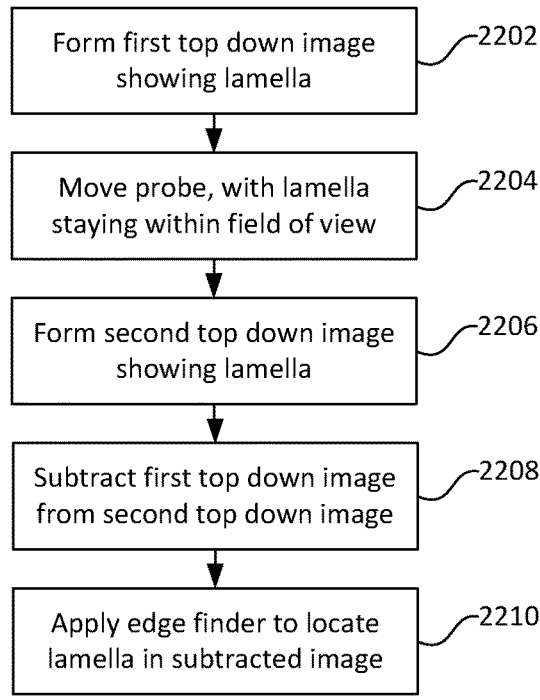
FIGS. 22a and 22b are flow charts showing an image subtraction method for determining the position of the lamella.
Figure 22B:
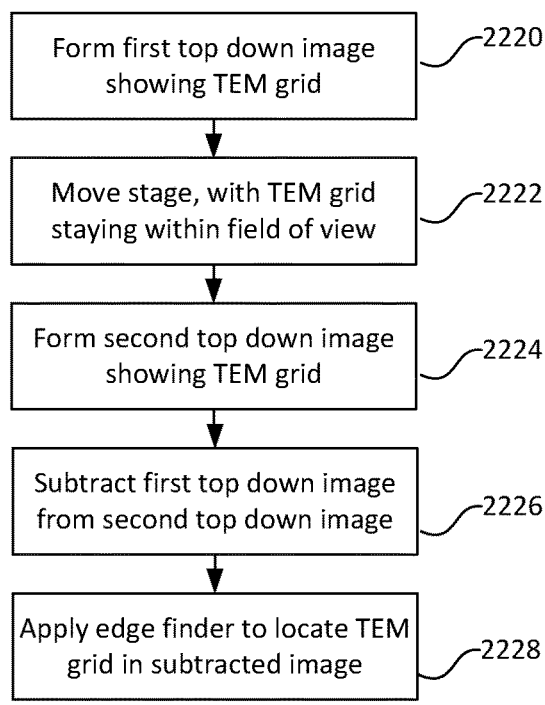
Figures 23A, 23B, 23C:
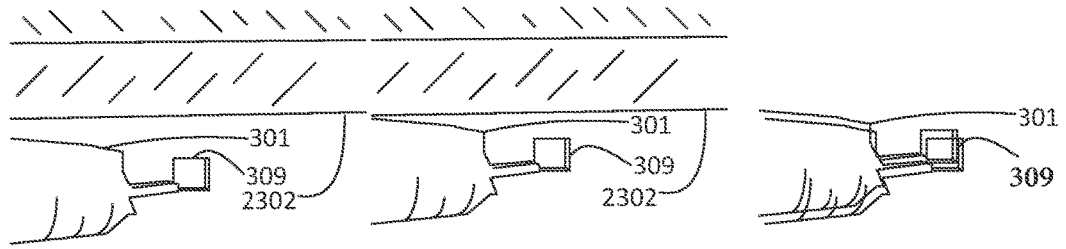
FIGS. 23a-23f show images used in an image subtraction for determining the position of the lamella and the TEM grid in top down views.

FIGS. 22a and 22b show the steps of locating the lamella using subtractive imaging. In step 2202 of FIG. 22a, a top down SEM image is acquired showing the lamella 309 on the end of the probe tip 301 as shown in FIG. 23a. TEM grid 2302 is visible in the image. In step 2204, the probe holding the lamella is moved a small distance in the x-y plane such that the lamella 301 remains within the field of view. In step 2206, another image as shown in FIG. 23b, the image of FIG. 23b is acquired using the system settings as were used to acquire FIG. 23a. In step 2208, the image of FIG. 23a is subtracted from the image of FIG. 23b, which results in the image of FIG. 23c. FIG. 23c shows the lamella 309 and probe tip 301 while eliminating much of the background and the TEM grid 2302. In step 2210, an edge finder or other metrology tool is applied to the subtracted image to precisely determine the position of the lamella.

Figures 23D, 23E, 23F:
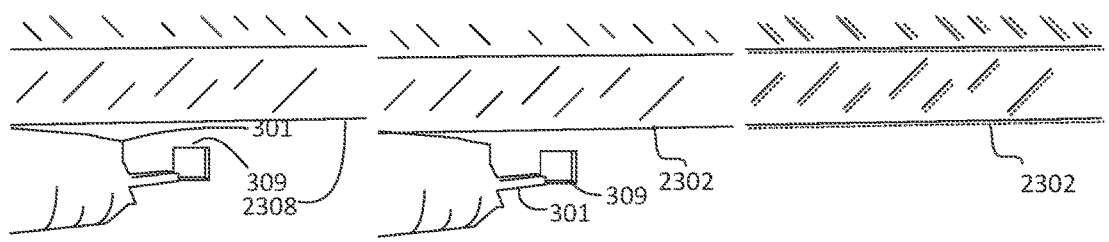

After determining the position of the lamella in the x-y plane, the position of the attachment point on the TEM grid is determined in step 2104 (FIG. 21). In step 2220 (FIG. 22b), a top down SEM image of the TEM grid 2302 is acquired as shown in FIG. 23d. In step 2222, the stage supporting the TEM grid is moved slightly such that the TEM grid remains within the field of view of FIG. 23d. In step 2224, a second image is acquired using the same beam settings as the first image. In step 2226, the first image shown in FIG. 23*d* is subtracted from the second image shown in FIG. 23*e*, resulting in the image of FIG. 23*f*. In step 2228, an edge finder or other metrology tool is applied to the subtracted image to precisely determine the position of the TEM grid 2302.

In step 2106, a vector $V_{XY}$ displacement is determined between the lamella 309 and the attachment point on the TEM grid 2412 as shown in FIG. 24. In step 2108, the lamella is moved in the X-Y plane to a position directly above the attachment point location.

In step 2110, the lamella is located using the other beam to provide a different perspective so that the Z dimension of the lamella can be determined. The lamella can be located, for example, using image recognition assisted by a fiducial 306 on the lamella, using an image subtraction technique, or both techniques.

Figures 26A, 26B, 26C:
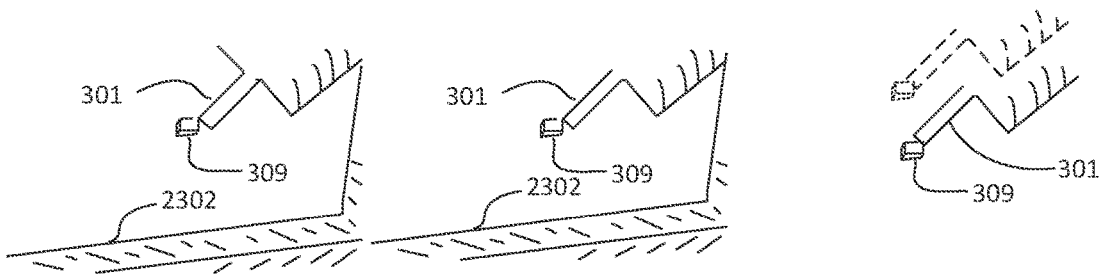
FIGS. 26a-26f show images used in an image subtraction for determining the difference in z coordinates of the lamella and the TEM grid in angled views.

FIGS. 25*a* and 25*b* are flow charts showing the steps of using image subtraction to determine the Z displacement. In step 2502, an angled FIB image is acquired showing the lamella as shown in FIG. 26*a*. In step 2504, the probe holding the lamella is moved a small distance in the Z direction such that the lamella remains within the field of view of the ion beam image. In step 2506, another image as shown in FIG. 26*b* is acquired, the image of FIG. 26*b* being acquired using the system settings as were used to acquire FIG. 26*a*. In step 2508, the image of FIG. 26*a* is subtracted from the image of FIG. 26*b*, which results in the image of FIG. 26*c*, which shows the lamella and probe while eliminating much of the background. In step 2510, an edge finder or other metrology tool is applied to the subtracted image to precisely determine the position of the lamella.

Figures 26D, 26E, 26F:
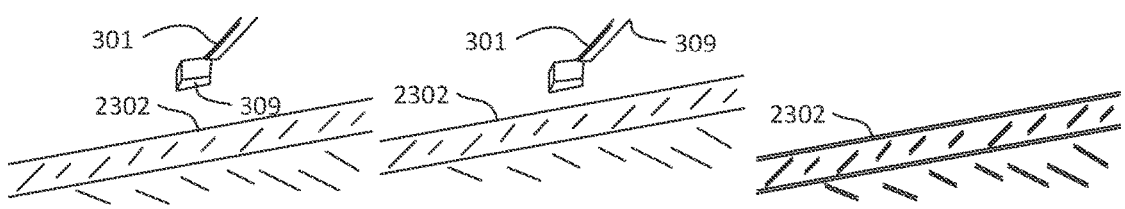

After determining the position of the lamella from the perspective of the FIB, the position of the attachment point in the TEM is determined from the perspective of the FIB in step 2112. In step 2520, an angled view of the TEM grid 2302 is acquired as shown in FIG. 26*d*. In step 2522, the stage that supports the TEM grid 2302 is moved a small amount in the Z direction such that the TEM grid 2302 remains within the field of view of FIG. 26*d*. In step 2526, the image of FIG. 26*d* is subtracted from FIG. 26*e*, resulting in the image of FIG. 26*f*. In step 2528, an edge finder or other metrology tool is applied to the subtracted image to precisely determine the position of the TEM grid.

In step 2114, a vector $V_z$, the difference in height between the lamella and the attachment point on the TEM grid, is determined using the distance between the lamella and the attachment point of the TEM grid in the FIB view, divided by sine of the angle between the FIB axis and a normal to the surface. In step 2116, the probe is moved the calculated distance, $V_z$ in the Z direction.

Figure 27:
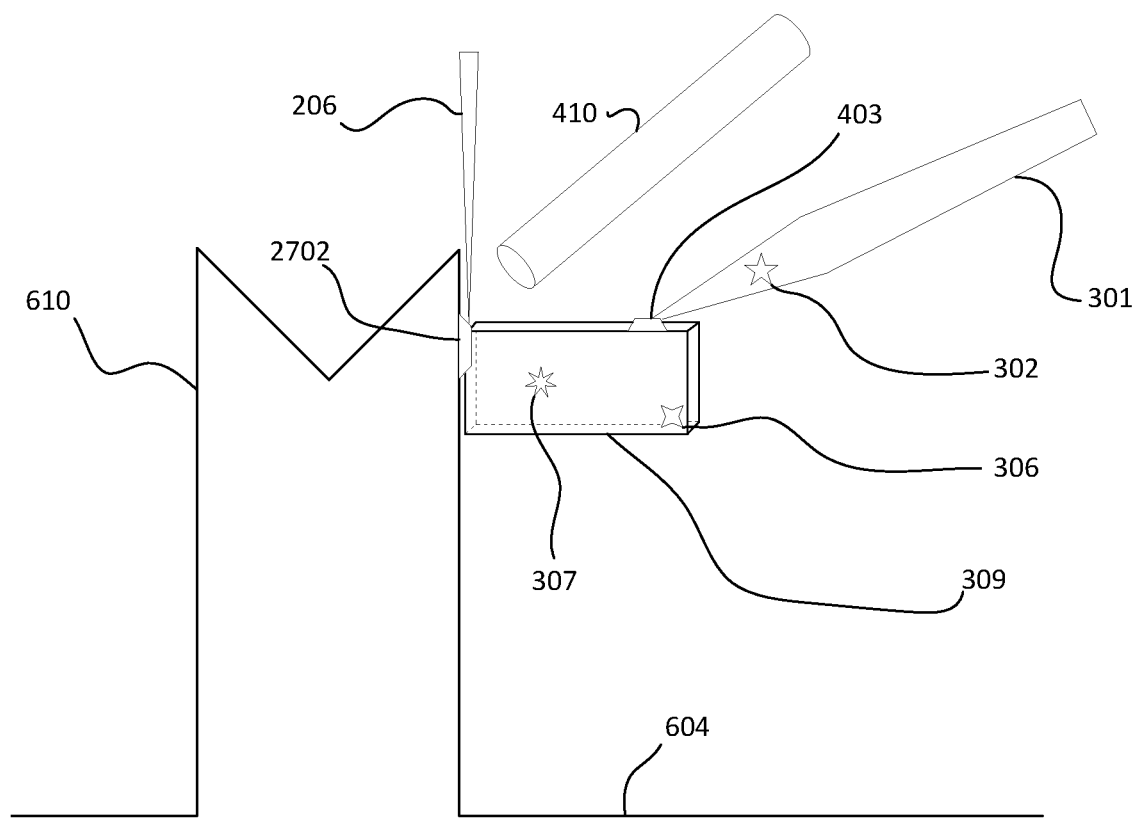
FIG. 27 shows a lamella being attached to a TEM grid.
Figure 28:
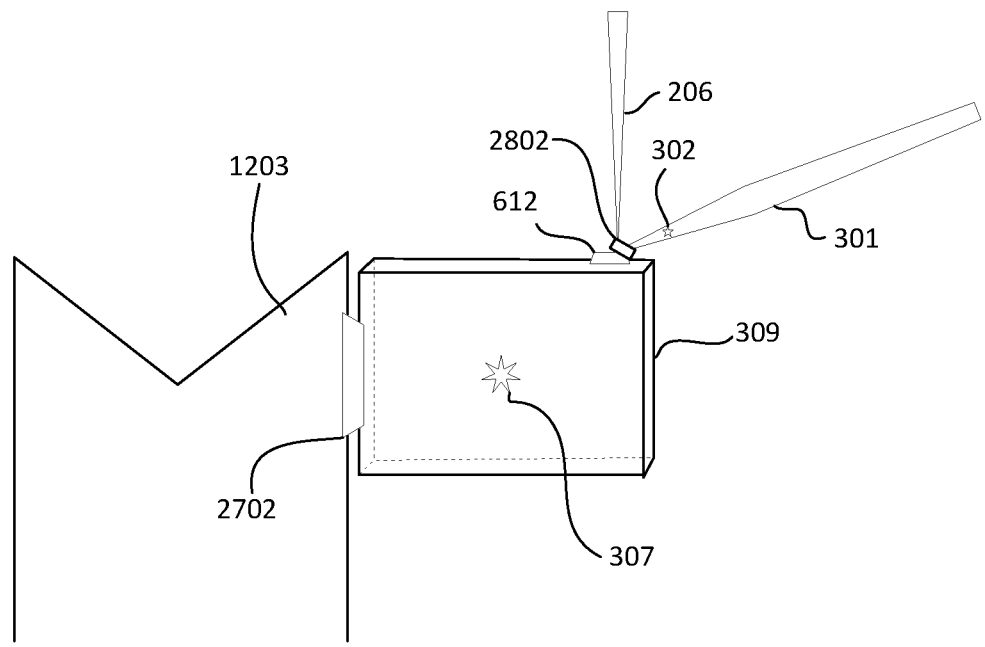
FIG. 28 show the probe being severed from a lamella attached to a TEM grid.
Figure 29:
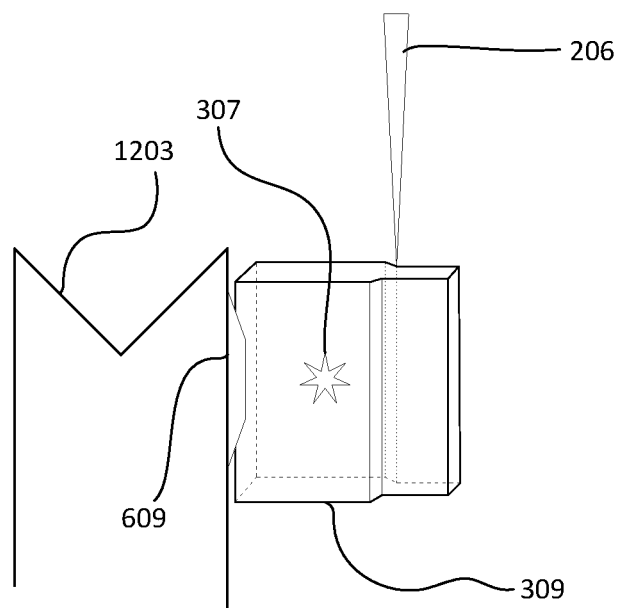
FIG. 29 shows a lamella attached to a TEM grid being thinned.

In step 2118, the lamella 309 is welded to the TEM grid 1302 as shown in FIG. 27. The ion beam 206 is used to decompose a precursor gas from gas injection needle 410 to deposit a weld material 2702 to attach the lamella 309. In step 2120, the ion beam is used to sever the probe 301 from the lamella 309 as shown in FIG. 28. Alternatively, the probe and lamella can be severed by moving them apart. A mill box 2802 is positioned to sever the connection between the lamella and the probe. In optional step 2124, a fiducial 302 is milled on the probe tip, as shown, for example, in FIG. 19, so that the probe tip can be more easily recognized by image recognition software during lift out of the next lamella. In optional step 2126, the lamella is thinned further while mounted on the TEM grid as shown in FIG. 29.

After forming a first lamella and moving it to the TEM grid, the process can be repeated for subsequent lamellae. In addition or alternatively, the probe tip is re-shaped as described in FIG. 6 before the probe tip approaches the next lamella for lift-out so that the probe tip is easily recognized by the automated image recognition software.

While two images are described above for an image subtraction routine, three or more images may also be used. Subtractive imaging allows identification of a specific object even in an area which would present false positives during image analysis.

Typical System for Carrying out the Methods

Figure 30:
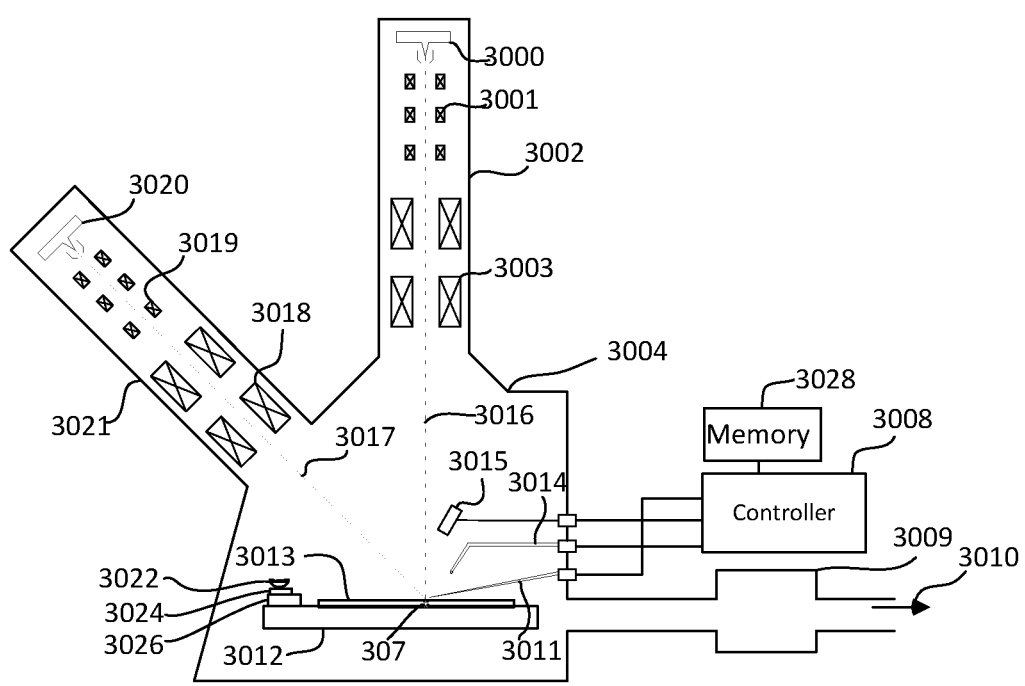
FIG. 30 shows a dual beam system suitable for carrying out the automated lamella preparation steps described herein.

FIG. 30 shows a typical dual charged particle beam system that can be used to perform the steps of different embodiments of the invention. The system has an electron beam column 3002, with electron source 3000 and beam shaping lenses 3001 and 3003, and directs electron beam 3016. The system also has an ion beam column 3021, with an ion source 3020, and ion focusing lenses 3019 and 3018, and directs ion beam 3017. The beams are directed towards a sample 3013 containing region of interest 307, the sample 3013 positioned on a 5-axis primary stage 3012 that can move in the x-y-z directions, rotate, and tilt. A TEM grid holder 3024 for holding TEM grids 3022 is mounted on the primary stage. Optionally, the TEM grid holder 3024 can be mounted on a secondary stage 3026 to prove additional degrees of freedom for manipulating the TEM grid for lamella attachment and for processing the lamella. The system also includes a particle detector 3015, a gas introduction system 3014, and a sample manipulation probe 3011, which can move the probe tip in the x-y-z direction as well as rotate about the probe axis. The charged particle beam columns, detector, gas introduction system, and sample manipulation probe are contained in a vacuum chamber 3004, which is pumped by vacuum pump 3009. The charged particle columns, detector, gas introduction system, and sample probe are controlled by a controller 3008, which can retrieve computer instructions stored on memory 3028.

Although the description of the present invention above is mainly directed at a method of producing TEM lamella, the method offering advantages in robustness, repeatability, and speed, and therefore suitable for automation, it should be recognized that an apparatus performing the operation of this method would be within the scope of the present invention. Further, it should be recognized that embodiments of the present invention can be implemented via computer hardware or software, or a combination of both. The methods can be implemented in computer programs using standard programming techniques, including a computer-readable storage medium configured with a computer program, where the storage medium so configured causes a computer to operate in a specific and pre-defined manner, according to the methods and figures described in this Specification. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits programmed for that purpose.

Further, methodologies may be implemented in any type of computing platform, including but not limited to, personal computers, mini-computers, mainframes, workstations, networked or distributed computing environments, computer platforms separate, integral to, or in communication with charged particle tools or other imaging devices, and the like. Aspects of the present invention may be implemented in machine readable code stored on a storage medium or device, whether removable or integral to the computing platform, such as a hard disk, optical storage media, RAM, ROM and the like, so that it is readable by a programmable computer, for configuring and operating the computer when the storage media or the device is read by the computer to perform the procedures described herein. Moreover, machine-readable code, or portions thereof, may be transmitted over a wired or wireless network or networks. The invention described herein includes these and other various types of computer-readable storage media when such media contain instructions or programs for implementing the steps described above in conjunction with a microprocessor or other data processor. The invention also includes the computer itself when programmed according to the method and techniques described herein.

Although much of the previous description is directed at semiconductor wafers, the invention could be applied to any suitable substrate or surface.

Some embodiments of the invention provide a method for automated sample preparation in a charged particle beam system, comprising:

loading a work piece into a vacuum chamber featuring one or more charged particle beam systems and a sample manipulation probe;

imaging the area of interest on the work piece;

removing material surrounding a thin section using a focused ion beam;

removing material supporting the thin section, leaving the thin section attached to the bulk work piece by small attachment structures;

shaping the tip of a sample manipulation probe by removing material using said ion beam;

moving said sample probe automatically into close proximity of said thin section;

attaching the sample probe to the thin section;

removing said support structure connecting the thin section to the bulk of the work piece using the ion beam, so that the thin section is supported only by the sample probe;

moving the sample probe, with the thin section attached, to a region where a sample grid for thin sections is located;

imaging of the region where the sample grid and the probe, with attached thin section, are located;

moving the probe automatically so that the thin section is in close proximity to the sample grid;

attaching the thin section to the sample grid; and removing the tip of the sample probe from the thin section.

In some embodiments, the thin section is a cross section view section.

Some embodiments use image analysis to direct the movement of the sample probe.

In some embodiments, the tip is shaped into a chisel shape.

Some embodiments include locating the probe using image analysis to determine a trajectory to move the probe to the thin section or to the sample grid.

In some embodiments, the image analysis uses image subtraction.

Some embodiments further comprise calculating an XY vector between said probe and said thin section based on images from one charged particle beam and a Z vector between said probe and said thin section based on images from a second particle beam.

In some embodiments, the method further comprises reshaping the tip after the thin section has been disconnected from the probe.

In some embodiments, the method further comprises attaching the probe to the face of the thin section away from a region of interest.

In some embodiments, the method further comprises thinning the thin section further after it has been attached to the sample grid.

Some embodiments of the invention provide an apparatus for automated sample production in a charged particle system comprising:

a vacuum chamber for containing a work piece;

at least two charged particle beam columns for producing charged particle beams for imaging and operating on the work piece within the vacuum chamber;

a moveable sample stage for holding and moving the work piece within the vacuum chamber;

a charged particle detector for forming images from charged particles emitted from the sample upon impact of the charged particle beams;

a sample manipulation probe capable of submicron positioning;

a gas injection system for providing a precursor gas for charged particle beam-induced deposition;

a controller for controlling the operation of the apparatus, a computer readable memory for storing computer instruction for execution by the controller for carrying out the method of claim 1.

In some embodiments, the apparatus further comprises an apparatus where there are two charged particle beam systems.

In some embodiments, the at least two charged particle beam columns for producing charged particle beams for imaging and operating on the work piece include an electron beam column and an ion beam column.

In some embodiments, the computer memory includes computer instructions for the analysis of images formed by the charged particle beams, the image analysis programed to locate said sample manipulation probe, with or without an attached thin section.

In some embodiments, the image analysis is performed using image subtraction.

In some embodiments, the means for material removal is a focused ion beam.

In some embodiments, the computer memory includes computer instructions to cause the focused ion beam to create fiducials on the thin section.

In some embodiments, the computer memory includes computer instructions to cause the focused ion beam to create a fiducial on the probe.

In some embodiments, the computer memory includes computer instructions to cause the focused ion beam to form the tip of the sample probe into a chisel shape.

Some embodiments of the invention provide a method for automated sample preparation in a charged particle beam system, comprising:

loading a work piece into a vacuum chamber including one or more charged particle beam systems and a sample manipulation probe;

automatically physically re-shaping the manipulation probe to a new shape;

automatically performing charged particle milling operations to form a sample from a portion of a work piece; and using the re-shaped probe to remove a sample from the work-piece.

In some embodiments, using the re-shaped probe to remove the sample from the work piece includes using image recognition software to automatically determine the position of the re-shaped probe.

In some embodiments, re-shaping the probe comprises forming a probe tip into rectangular prism.

Some embodiments of the invention provide a method for automated sample preparation in a charged particle beam system, comprising:

loading a work piece into a vacuum chamber including one or more charged particle beam systems and a sample manipulation probe;

forming a fiducial on the manipulation probe;

performing charged particle beam milling operations to form a sample from a portion of a work piece;

using automated image recognition to identify the fiducial on the manipulator probe to determine the position of the manipulator probe;

automatically moving the manipulator probe from the position determined by the image recognition software to a position adjacent the sample;

attaching the probe to the sample; and removing the sample from the work piece.

In some embodiments, the lamella has a thickness of less than 100 nm.

In some embodiments, attaching the probe to the sample includes attaching the probe to the sample using charged particle beam-induced deposition.

In some embodiments provide a method for automated sample preparation in a charged particle beam system, comprising:

loading a work piece into a vacuum chamber including one or more charged particle beam systems and a sample manipulation probe;

performing charged particle beam milling operations to form a sample from a portion of a work piece;

forming a fiducial on the sample;

attached the probe to the sample;

removing the sample from the work piece;

using automated image recognition to identify the fiducial on the sample to determine the position of the sample relative to a sample holder; and automatically moving the sample to the sample holder using the position of the sample determined by the automated image recognition.

In some embodiments, forming a fiducial on the sample includes directing a charged particle beam toward the sample to form the fiducial.

In some embodiments, the sample is a lamella having a thickness of less than 100 nm and in which forming a fiducial on the sample includes directing a charged particle beam toward the lamella to form the fiducial.

In some embodiments, automatically moving the sample to the sample holder using the position of the sample determined by the automated image recognition includes automatically moving the sample to a TEM grid and further comprising attaching the sample to the TEM grid using beam-induced deposition.

Some embodiments provide a method for automated sample preparation in a charged particle beam system, comprising:

loading a work piece into a vacuum chamber including one or more charged particle beam systems and a sample manipulation probe;

automatically performing charged particle milling operations to form a sample from a portion of a work piece;

forming an image of a portion of the manipulator probe;

moving the manipulator probe;

forming a second image of the manipulator probe;

forming a differential image showing the differences between the first image and the second image;

using image recognition software, locate the manipulator probe in the differential image to determine the position of the manipulator probe;

using the determined position, moving the manipulator probe to the sample; and attaching the sample to the manipulator probe.

In some embodiments, the sample comprises a lamella having a thickness of less than 100 nm.

In some embodiments, moving the manipulator probe to the sample comprises moving the manipulator probe into contact with the lamella or sufficiently close to the lamella to attach the manipulator probe to the lamella using charged particle beam-induced deposition.

Some embodiments provide a method for automated preparation in a charged particle beam system of a sample for viewing a region of interest in a transmission electron microscope, comprising:

identifying a region of interest in the work piece in a vacuum chamber;

directing an ion beam toward the work piece to remove material from either side of the region of interest to leave a lamella having a thickness of less than 100 nm containing the region of interest;

forming a first charged particle beam image of a manipulator probe above the work piece;

moving the manipulator;

forming a second charged particle beam image of the manipulator probe above the work piece;

determining a third image representing a difference between the first image and the second image;

automatically recognizing the manipulator probe in the third image to determine the position of the probe;

determining a trajectory to bring the manipulator probe in contact with or in proximity to the lamella;

moving the manipulator into contact with, or into proximity to, the lamella;

directing a precursor gas toward the manipulator probe;

directing the ion beam to decompose the precursor gas to deposit a material to connect the manipulator probe to the lamella;

freeing the lamella from the work piece;

moving the probe with the lamella to a TEM grid;

attaching the lamella to the TEM grid; and freeing the probe from the lamella, in which the third image representing a difference between the first image and the second image reduces elements associated with the work piece in the first and second image to facilitate recognition of the manipulator probe in the third image.

In some embodiment, forming a first charged particle beam image of a manipulator probe above the work piece includes forming a first top down image;

moving the manipulator includes moving the manipulator in the x-y plane;

forming a second charged particle beam image of the manipulator probe above the work piece includes forming a second top down image;

determining a third image representing a difference between the first image and the second image;

automatically recognizing the manipulator probe in the third image to determine the position of the probe includes determining the x-y coordinates of the manipulator probe;

determining a trajectory to bring the manipulator probe in contact with or in proximity to the lamella includes determining a trajectory to move the manipulator in an x-y plane to a point above the place where the manipulator is to be attached to the lamella;

and further comprising:

forming a third charged particle beam image of a manipulator probe from a charged particle beam that is not orthogonal to the surface;

moving the manipulator probe in the z plane;

forming a fourth charged particle beam image of a manipulator probe from a charged particle beam that is not orthogonal to the surface;

determining a fifth image representing a difference between the third image and the fourth image;

automatically recognizing the manipulator probe in the fifth image to determine the position of the probe in the Z direction; and determining a trajectory to bring the manipulator probe in contact with or in proximity to the lamella further includes determining a trajectory to move the manipulator in the z direction to a point above the place where the manipulator is to be attached to the lamella.

In some embodiments:

forming a first charged particle beam image including forming a first electron beam image;

forming a second charged particle beam image includes forming a second electron beam image;

forming a third charged particle beam image of a manipulator probe includes forming an ion beam image; and forming a fourth charged particle beam image of a manipulator probe includes forming an ion beam image.

Some embodiments provide a method for automated preparation in a charged particle beam system of a sample for viewing a region of interest in a transmission electron microscope:

repeating the steps of the method for automated preparation in a charged particle beam of a sample for viewing a region of interest in a transmission electron microscope;

between each repetition, milling the probe tip with the ion beam to form the same specified shape during each repetition, the specified shape recognizable by image recognition software; and in which automatically recognizing the manipulator probe in the third image to determine the position of the probe during each repetition of the steps includes recognizing the specified shape.

In some embodiments, forming the same specified shape recognizable by image recognition software includes forming an end edge at the end of the probe, the end edge forming a non-normal angle to longitudinal axis of the probe.

Some embodiments provide a method of automatically shaping the tip a micromanipulator probe used for preparing a thin sample for viewing on a TEM including a needle, a tip extending from the needle and having a diameter smaller than that of the needle, and a shoulder between the needle and the tip, comprising:

locating the end of the tip;

locating the shoulder;

locating a desired tip start position along the needle so that the distance from the desired tip start position to the end of the tip corresponds to a desired tip length;

automatically removing with the ion beam first material from the needle from the desired tip start position to at least the shoulder;

automatically milling with the ion beam to produce smooth surface from the tip start position to the end of the tip;

rotating the manipulator;

automatically removing with the ion beam second material from the needle from the desired tip start position to at least the shoulder; and automatically milling with the ion beam to produce smooth surface from the tip start position to the end of the tip.

In some embodiments locating the shoulder comprises automatically locating in the image the top edge of the needle and determining the point at which the top edge of the needle stops.

In some embodiments:

automatically removing with the ion beam first material from the needle includes removing a first portion of the first material and removing a second portion of the first material, the first portion and the second portion of the first material separate by a distance corresponding to a desired tip thickness in a first dimension; and automatically removing with the ion beam first material from the needle includes removing a first potion of the second material and removing a second portion of the second material, the first portion and the second portion of the first material separate by a distance corresponding to a desired tip thickness in a second dimension.

In some embodiments the first and second portion of the first material are on opposite sides of the needle axis and the first and second portion of the second material are on opposite sides of the needle axis.

Some embodiments provide a method of automatically shaping the tip a micromanipulator probe used for preparing a thin sample for viewing on a TEM including a needle, a tip extending from the needle and having a diameter smaller than that of the needle, and a shoulder between the needle and the tip, comprising:

a) locating the end of the tip in a charged particle beam image;

b) using an edge locator tool, locate the top edge of the needle in the image;

c) using an edge locator tool, locate the bottom edge of the needle in the image;

d) determining from the top edge of the needle and the bottom edge of the needle the location of the needle axis;

e) moving an edge locator tool along the needle in the direction of the tip end to determine the position of a shoulder at the end of the top edge of the needle;

f) milling a first region of the needle offset in a first direction by a desired needle thickness from the needle axis, beginning from the shoulder or before the shoulder to a specified distance from the end of the needle tip, the specified distance corresponding to a desired tip length;

g) milling a second region of the needle offset in a second direction by a desired needle thickness from the needle axis, beginning from the shoulder or from before the shoulder to a specified distance from the end of the needle tip, the specified distance corresponding to a desired tip length;

h) rotating the needle; and i) repeating steps b-g.

In some embodiments, the method further comprises cutting the end of the tip at an angle that is not orthogonal angle to the needle axis.

Some embodiments provide a method for automated preparation in a charged particle beam system of a sample for viewing a region of interest in a transmission electron microscope, comprising:

loading a work piece into a vacuum chamber of the charged particle beam having one or more charged particle beam systems and a sample manipulation probe;

identifying a region of interest in the work piece;

directing an ion beam toward the work piece to remove material from either side of the region of interest to leave a lamella having a thickness of less than 100 nm containing the region of interest;

directing the ion beam to form a fiducial on the lamella;

attaching the manipulator to the lamella;

freeing the lamella from the work piece;

moving the probe with the lamella to the vicinity of a TEM grid;

using image recognition software to recognize the fiducial in the lamella;

using the position of the fiducial in the lamella to determine a trajectory to move the lamella to attachment point at the TEM grid; and attaching the lamella to the TEM grid.

In some embodiments directing the ion beam to form a fiducial on the lamella includes milling a shaped hole in the lamella.

In some embodiments directing the ion beam to form a fiducial on the lamella includes milling a shape in the surface of the lamella.

Some embodiments provide a method for automated sample preparation in a charged particle beam system in which a micromanipulator probe is attached to a lamella and used to transport the lamella, comprising:

loading a work piece into a vacuum chamber featuring one or more charged particle beam systems and a sample manipulation probe;

identifying an area of interest on the work piece;

removing material around the region of interest to leave a thin section including the region of interest;

directing the ion beam to create a fiducial on the tip of the probe, so that the tip may be identified by an automatic system;

forming an image of the probe tip that includes the fiducial;

using image recognition software, identifying the fiducial in the image;

using the location of the fiducial determine by the image recognition software, determine a displacement vector between the probe tip and an attachment point on the lamella;

moving the probe tip in accordance with the displacement vector to bring the probe tip into contact with or proximity with the lamella;

attaching the probe tip to the lamella;

severing the lamella from the work piece;

moving the probe tip with the lamella attached to a TEM grid;

attaching the lamella to the TEM grid; and severing the probe from the lamella.

Whenever a scan or image is being processed automatically using computer processing, it should be understood that the raw image data can be processed without ever generating an actual viewable image. The term "image" is used in a broad sense to include not only a displayed image showing the appearance of the surface, but also to include any collection of information characterizing the multiple points on or below a surface. For example, a collection of data corresponding to the secondary electrons collected when a particle beam is incident on a series of points on the surface is a type of "image", even if the data is not displayed. Collecting information about points on the sample or the work piece is "imaging." The term "automatic" or "automatically" means without operator intervention, but does not require that every step of an operation be performed without operator intervention or that a process begin without operator intervention.

Preferred embodiments of the present invention make use of a particle beam apparatus, such as a FIB or SEM, in order to image a sample using a beam of particles. Such particles used to image a sample inherently interact with the sample resulting in some degree of physical transformation. Further, throughout the present Specification, discussions utilizing terms such as "calculating", "determining", "measuring", "generating", "detecting", "forming" or the like, also refer to the action and process of a computer system, or similar electronic device, that manipulates and transforms data represented as physical quantities within the computer system into other data similarly represented as physical quantities within the computer system or other information storage, transmission, or display devices.

The invention has broad applicability and can provide many benefits as described and shown in the examples above. The embodiments will vary depending on the specific application, and not every embodiment will provide all of the benefits and meet all of the objectives that are achievable by the invention.

In the following discussion and in the claims, the terms "including" and "comprising" are used in the open-ended fashion, and thus should be interpreted to mean "including, but not limited to . . . ". The term "focused ion beam" is used herein to refer to any collimated ion beam, including beams focused by ion optics and shaped ion beams.

To the extent that any term is not specially defined in this Specification, the intent is that the term is to be given its plain and ordinary meaning. The accompanying drawings are intended to aid in understanding the present invention and, unless otherwise indicated, are not drawn to scale.

Although the present invention and its advantages have been described in detail, it should be understood that various changes, substitutions, and alterations can be made to the embodiments described herein without departing from the scope of the invention as defined by the claims. Moreover, the scope of the present application is not intended to be limited to the particular embodiments of matter, means, methods, and steps described in the specification.

We claim as follows:

1. A method for automated sample preparation in a charged particle beam system, comprising:

loading a work piece into a vacuum chamber including one or more charged particle beam columns and a sample manipulation probe;

performing charged particle beam milling operations to form from a portion of the work piece a sample for observation on a transmission electron microscope;

after performing charged particle beam milling operations to form from the portion of the work piece the sample, forming one or more fiducials on the formed sample;

attaching the sample manipulation probe to the sample;

removing the sample from the work piece; and using the one or more fiducials on the removed sample to determine a position and/or a rotational alignment of the sample.

2. The method of claim 1 in which forming a fiducial on the sample includes directing a charged particle beam toward the sample to form the fiducial.

3. The method of claim 1 in which the sample is a lamella having a thickness of less than 200 nm and in which forming a fiducial on the sample includes directing a charged particle beam toward the lamella to form the fiducial.

4. The method of claim 1 in which using the one or more fiducials on the sample to determine the position and/or a rotational alignment of the sample includes automatically moving the sample to a TEM grid and attaching the sample to the TEM grid using beam-induced deposition.

5. The method of claim 1 further comprising using the position and/or rotational alignment determined using the fiducials in a subsequent processing or imaging step.

6. The method of claim 1 further comprising positioning and/or rotationally aligning the sample using the position and/or rotational alignment determined using the fiducials.

7. The method of claim 1 in which the one or more fiducials comprises multiple fiducials.

8. The method of claim 1 in which the one or more fiducials comprises a single fiducial.

9. The method of claim 1 in which positioning and/or rotationally aligning the sample for further processing comprises positioning and/or aligning the sample with a TEM grid further comprising attaching the sample to the TEM grid.

10. The method of claim 1 in which:
using the one or more fiducials on the sample to determine the position and/or the rotational alignment of the sample includes using the one or more fiducials on the sample to determine the rotational alignment of the sample; and
positioning or rotationally aligning the sample using the one or more fiducials comprises rotationally aligning the sample using the one or more fiducials.

11. The method of claim 1 in which using the one or more fiducials on the sample to determine the position or rotational alignment of the sample comprises using image recognition software to recognize the one or more fiducials.

12. The method of claim 1 in which positioning or rotationally aligning the sample using the one or more fiducials comprises moving the sample to a sample holder using the one or more fiducials.

13. The method of claim 1 in which forming one or more fiducials on the sample comprises etching the sample using charged particle beam etching to form the one or more fiducials.

14. The method of claim 1 in which forming one or more fiducials on the sample comprises depositing material using charged particle beam-induced deposition to form the one or more fiducials.

15. The method of claim 1 in which forming one or more fiducials on the sample comprises forming one or more fiducials adjacent to a region of interest.

16. The method of claim 1 in which using the one or more fiducials on the sample to determine a position and/or a rotational alignment of the sample comprises using the one or more fiducials during thinning of the sample to determine how features evolve as the sample is thinned.

17. The method of claim 1 in which forming one or more fiducials on the sample comprises forming one or more shapes on, or holes in, the sample.

18. The method of claim 1 in which positioning or rotationally aligning the sample using the one or more fiducials comprises using the one or more fiducials on the sample to guide the sample to a TEM grid for attachment.

19. The method of claim 1, wherein the sample comprises a lamella, and the forming one or more fiducials on the formed sample comprises forming one or more fiducials on a face, rather than the top, of the lamella.

20. A method for automated preparation in a charged particle beam system of a sample for viewing a region of interest in a transmission electron microscope, comprising:
loading a work piece into a vacuum chamber of the charged particle beam system having one or more charged particle beam columns and a sample manipulation probe;
identifying a region of interest in the work piece;
directing an ion beam toward the work piece to remove material from either side of the region of interest to leave a lamella having a thickness of less than 100 nm containing the region of interest;
after directing an ion beam toward the work piece to remove material from either side of the region of interest to leave a lamella having a thickness of less than 100 nm containing the region of interest; directing the ion beam to form one or more fiducials on the lamella;
attaching the sample manipulation probe to the lamella;
freeing the lamella from the work piece;
moving the sample manipulation probe with the lamella to the vicinity of a TEM grid;
using image recognition software to recognize the one or more fiducials in the lamella;
using a position of the one or more fiducials in the lamella to determine a trajectory to move the lamella to an attachment point at the TEM grid; and
attaching the lamella to the TEM grid.

21. The method of claim 20 in which directing the ion beam to form a fiducial on the lamella includes milling a shaped hole in the lamella.

22. The method of claim 20 in which directing the ion beam to form a fiducial on the lamella includes milling a shape in a surface of the lamella.

23. The method of claim 20 further comprising rotationally aligning the lamella with the TEM grid using the one or more fiducials.

24. The method of claim 20, wherein the directing the ion beam to form one or more fiducials on the lamella comprises directing the ion beam to form one or more fiducials on a face, rather than the top, of the lamella.

* * * * *